US012042334B2

(12) United States Patent
Firouzi et al.

(10) Patent No.: US 12,042,334 B2
(45) Date of Patent: Jul. 23, 2024

(54) METHODS AND APPARATUS FOR PULSATILITY-MODE SENSING

(71) Applicant: Liminal Sciences, Inc., Guilford, CT (US)

(72) Inventors: Kamyar Firouzi, San Jose, CA (US); Guillaume David, Palo Alto, CA (US); Yichi Zhang, Mountain View, CA (US); Jose Camara, Saratoga, CA (US); Mohammad Moghadamfalahi, San Jose, CA (US)

(73) Assignee: Liminal Sciences, Inc., Guilford, CT (US)

( * ) Notice: Subject to any disclaimer, the term of this patent is extended or adjusted under 35 U.S.C. 154(b) by 242 days.

(21) Appl. No.: 17/387,763

(22) Filed: Jul. 28, 2021

(65) Prior Publication Data

US 2022/0031281 A1  Feb. 3, 2022

Related U.S. Application Data

(60) Provisional application No. 63/058,137, filed on Jul. 29, 2020.

(51) Int. Cl.
*A61B 8/08* (2006.01)
*A61B 8/02* (2006.01)
(Continued)

(52) U.S. Cl.
CPC .............. *A61B 8/5223* (2013.01); *A61B 8/02* (2013.01); *A61B 8/0816* (2013.01); *A61B 8/488* (2013.01);
(Continued)

(58) Field of Classification Search
CPC ... G06T 7/0016; A61B 8/0808; A61B 8/0816; A61B 8/52–5223
See application file for complete search history.

(56) References Cited

U.S. PATENT DOCUMENTS 6,014,473 A * 1/2000 Hossack ................. G06T 7/246
600/463
6,695,784 B1 * 2/2004 Michaell .............. A61B 8/0808
600/453
(Continued)

FOREIGN PATENT DOCUMENTS

WO   WO 2020/146880 A1   7/2020

OTHER PUBLICATIONS

Penfield, Wilder, Kálmán von Sántha, and Andr Cipriani. "Cerebral blood flow during induced epileptiform seizures in animals and man." Journal of Neurophysiology 2.4 (1939): 257-267.*
(Continued)

*Primary Examiner* — Carolyn A Pehlke
(74) *Attorney, Agent, or Firm* — Foley & Lardner LLP

(57) ABSTRACT

According to some aspects, there is provided a device configured to determine a measure of brain tissue motion in a brain, comprising: at least one transducer configured to transmit an acoustic signal to at least one region of the brain and receive a subsequent acoustic signal from the at least one region of the brain; and at least one processor configured to: determine the measure of brain tissue motion in the at least one region of the brain by processing the subsequent acoustic signal, wherein processing the subsequent acoustic signal comprises filtering the subsequent acoustic signal. Filtering the subsequent acoustic signal may comprise one of spatiotemporal filtering, signal decomposition, tissue tracking, and/or spectral clustering.

1 Claim, 31 Drawing Sheets

(51) Int. Cl.
*B06B 1/02* (2006.01)
*B06B 1/06* (2006.01)
(52) U.S. Cl.
CPC .......... *A61B 8/5207* (2013.01); *B06B 1/0292* (2013.01); *B06B 1/06* (2013.01)

(56) References Cited

U.S. PATENT DOCUMENTS

2005/0074154 A1* 4/2005 Georgescu .............. G06T 7/251
382/128
2008/0275340 A1* 11/2008 Beach .................. A61B 8/0808
600/438
2019/0196013 A1 6/2019 Stanziola et al.

OTHER PUBLICATIONS

Mills, David M. "Medical imaging with capacitive micromachined ultrasound transducer (cMUT) arrays." IEEE Ultrasonics Symposium, 2004. vol. 1. IEEE, 2004.*
Mauldin, F. William, Dan Lin, and John A. Hossack. "The singular value filter: A general filter design strategy for PCA-based signal separation in medical ultrasound imaging." IEEE transactions on medical imaging 30.11 (2011): 1951-1964.*
International Search Report and Written Opinion mailed Nov. 4, 2021 in connection with International Application No. PCT/US2021/043517.

* cited by examiner

METHODS AND APPARATUS FOR PULSATILITY-MODE SENSING

CROSS-REFERENCE TO RELATED APPLICATIONS

This application claims the benefit under 35 U.S.C. § 119(e) of U.S. provisional patent application Ser. No. 63/058,137, entitled "METHODS AND APPARATUS FOR MONITORING BRAIN HEALTH AND CONDITIONS", filed Jul. 29, 2020, which is hereby incorporated by reference in its entirety herein.

BACKGROUND

Non-invasive monitoring of the brain typically relies on transcranial ultrasound devices. Such devices are typically limited in frame rate and are bulky and expensive. Further, their performance has a high level of uncertainty and questionable accuracy. Moreover, such devices are not easy to use and require an operator who has been specially trained on how to place the probe and identify the right location of the brain.

SUMMARY

According to some aspects, there is provided a device configured to determine a measure of brain tissue motion in a brain, comprising: at least one transducer configured to transmit an acoustic signal to at least one region of the brain and receive a subsequent acoustic signal from the at least one region of the brain; and at least one processor configured to: determine the measure of brain tissue motion in the at least one region of the brain by processing the subsequent acoustic signal, wherein processing the subsequent acoustic signal comprises filtering the subsequent acoustic signal.

According to some embodiments, there is provided a method for determining a measure of brain tissue motion in a brain, comprising: transmitting, with at least one transducer, an acoustic signal to at least one region of the brain; receiving, with the at least one transducer, a subsequent acoustic signal from the at least one region of the brain; and determining the measure of brain tissue motion in the at least one region of the brain by processing the subsequent acoustic signal, wherein processing the subsequent acoustic signal comprises filtering the subsequent acoustic signal.

According to some embodiments, there is provided a method for determining a measure of brain tissue motion in a brain, comprising: receiving a subsequent acoustic signal from at least one region of the brain; and determining the measure of brain tissue motion in the at least one region of the brain at least in part by applying a spatiotemporal filter to the subsequent acoustic signal.

According to some embodiments, there is provided a method for determining a measure of brain tissue motion in a brain, comprising: receiving a subsequent acoustic signal from at least one region of the brain; and determining the measure of brain tissue motion in the at least one region of the brain at least in part by filtering the subsequent acoustic signal, wherein filtering the subsequent acoustic signal comprises decomposing the subsequent acoustic signal into a plurality of component signals.

According to some embodiments, there is provided a method for determining a measure of brain tissue motion in a brain, comprising: receiving a subsequent acoustic signal from at least one region of the brain; and determining the measure of brain tissue motion in the at least one region of the brain at least in part by tracking a feature of the brain tissue over a period of time based on a plurality of images and/or measurements generated from the subsequent acoustic signal.

According to some embodiments, there is provided a method for determining a measure of brain tissue motion in a brain, comprising: receiving a subsequent acoustic signal from at least one region of the brain; and determining the measure of brain tissue motion in the at least one region of the brain at least in part by filtering the subsequent acoustic signal, wherein filtering the subsequent acoustic signal comprises: generating a plurality of images from the subsequent acoustic signal; based on a first image of the plurality of images, grouping pixels at different spatial locations in the first image into a first group of pixels; and determining an average temporal signal of the group of pixels across the plurality of images.

BRIEF DESCRIPTION OF THE DRAWINGS

Various aspects and embodiments will be described with reference to the following figures. It should be appreciated that the figures are not necessarily drawn to scale. For purposes of clarity, not every component may be labeled in every drawing. In the drawings.

DETAILED DESCRIPTION

I. Introduction

Figure 1A:
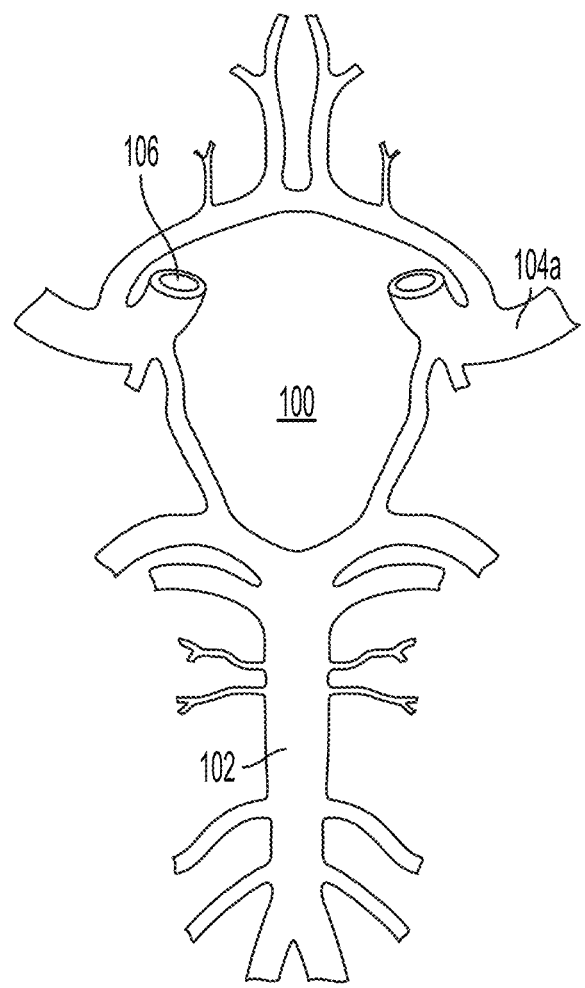
FIGS. 1A-1C show the Circle of Willis and its location in the brain.

Aspects of the technology described herein relate to methods and systems for sensing and monitoring motion and/or pulsatility in brain tissue and/or the cerebral vasculature. In some embodiments, the techniques may be performed non-invasively.

The inventors have recognized that there is a need for techniques capable of measuring brain tissue motion that are efficient, accurate, and affordable. Accordingly, described herein are techniques for extracting brain tissue motion from a set of images (e.g., a set of images acquired by acoustic sensing) which can be performed non-invasively and in real-time, which provide accurate results. A measure of pulsatility of the brain may be determined based on the extracted motion. The techniques described herein for measuring motion and pulsatility in the brain may be referred to herein as "pulsatility mode" or "p-mode" sensing, although, in some aspects, brain tissue motion alone is extracted.

The pulsatility mode measurements may be used in a number of applications. For example, in some embodiments, the pulsatility mode measurements may be used to provide compartmental (e.g., localized) measurements and analysis of a patient's brain health. In some embodiments, the pulsatility mode measurements may be used to map a metric over the entire brain.

Metrics that can be monitored using the pulsatility mode measurements include intracranial pressure, cerebral blood flow, and intracranial elastance. Such monitoring may enable characterization of brain tissue integrity in a wide range of neurological diseases in which changes in the biomechanical properties of the brain can lead to dramatic changes in pressure and flow dynamics, and hence tissue motion. The pulsatility mode sensing may also provide a fast means of revealing subtle physiological variations of the brain and potentially other tissues Additionally, the pulsatility mode measurements may be used for continuous monitoring of brain health and brain conditions; rapid screening of brain vitals and health in the field; and/or tracking autocompensatory and/or autoregulatory processes in the brain.

The inventors have recognized that existing techniques for monitoring the brain are insufficiently reliable. For example, transcranial doppler ultrasound (TCD) is one technique that may be used to measure the velocity of blood flow through the brain's blood vessels. TCD, however, is limited in frame rate, bulky, and expensive. TCD systems are limited to only measuring blood velocity in the vasculature at the base of the brain and therefore cannot provide a measurement of brain tissue motion or pulsatility in brain tissue. Additionally, the performance of TCD systems has a high level of uncertainty and questionable accuracy, as the location and angle with respect to the vessels are difficult to determine accurately. Lastly, TCD technologies are difficult to use, that is, the operator should have been trained on how to place the probe and identify the right location of the vessels around the Circle of Willis. For continuous monitoring, dedicated TCD systems often provide a robotic arm and headset that can automatically adjust the probe (mechanically) to assure a good quality signal, however, this feature comes at a high selling price.

Accordingly, the inventors have developed techniques for determining a measure of brain tissue motion. According to some embodiments there is provided a device configured to determine a measure of brain tissue motion in a brain, comprising: at least one transducer (e.g., a single transducer, a plurality of transducers, at least one capacitive micromachined ultrasonic transducer) configured to transmit an acoustic signal to at least one region of the brain and receive a subsequent acoustic signal from the at least one region of the brain; and at least one processor configured to: determine the measure of brain tissue motion in the at least one region of the brain by processing the subsequent acoustic signal, wherein processing the subsequent acoustic signal comprises filtering the subsequent acoustic signal.

In some embodiments, the subsequent acoustic signal is a reflection of the acoustic signal transmitted by the at least one transducer.

In some embodiments, the at least one processor is configured to determine a measure of pulsatility of the brain tissue based on the measure of brain tissue motion.

In some embodiments, the device further comprises transmit circuitry configured to control the at least one transducer to transmit the acoustic signal. The transmit circuitry may be configured to control the plurality of transducers to perform beam steering, at least in part by adjusting a timing of signals provided to the plurality of transducers.

In some embodiments, the device is wearable by or attached to or implanted within a subject being imaged.

In some embodiments, the brain tissue motion is caused at least in part by a seizure, and the at least one processor is configured to detect the seizure based on the measure of brain tissue motion. In some embodiments, the at least one processor is configured to determine a periodic pattern of brain tissue motion.

In some embodiments, processing the subsequent acoustic signal comprises determining a shift in a carrier frequency and/or a phase of one or more waveforms of the subsequent acoustic signal.

In some embodiments, filtering the subsequent acoustic signal comprises applying a spatiotemporal filter to the subsequent acoustic signal. Applying the spatiotemporal filter may comprise extracting the measure of brain tissue motion using singular value decomposition from a plurality of images generated from the subsequent acoustic signal.

In some embodiments, filtering the subsequent acoustic signal comprises decomposing the subsequent acoustic signal into a plurality of component signals. Decomposing the subsequent acoustic signal may be performed using kernel principal component analysis. In some embodiments, decomposing the subsequent acoustic signal may be performed using blind source separation.

In some embodiments, filtering the subsequent acoustic signal comprises tracking a feature of the brain tissue over a period of time based on a plurality of images and/or measurements generated from the subsequent acoustic signal. Tracking the feature of the brain tissue over the period of time may comprise determining a measure of similarity between consecutive images of the plurality of images. In some embodiments, the feature may comprise a distance between two points in the brain tissue, a surface area of the brain tissue, and/or a volume of the brain tissue.

In some embodiments, filtering the subsequent acoustic signal comprises: (1) generating a plurality of images from the subsequent acoustic signal; (2) based on a first image of the plurality of images, grouping pixels at different spatial locations in the first image into a first group of pixels; and (3) determining an average temporal signal of the group of pixels across the plurality of images.

In some embodiments, the at least one processor is further configured to determine a measure of intracranial pressure and/or a measure of intracranial elastance based on the measure of brain tissue motion.

According to some aspects, the techniques described herein may be embodied in the form of a method. For example, in some embodiments there is provided a method for determining a measure of brain tissue motion in a brain, comprising: transmitting, with at least one transducer, an acoustic signal to at least one region of the brain; receiving, with the at least one transducer, a subsequent acoustic signal from the at least one region of the brain; and determining the measure of brain tissue motion in the region of the brain by processing the subsequent acoustic signal, wherein processing the subsequent acoustic signal comprises filtering the subsequent acoustic signal.

According to some aspects there is provided a method for determining a measure of brain tissue motion in a brain, comprising: receiving a subsequent acoustic signal from at least one region of the brain; and determining the measure of brain tissue motion in the at least one region of the brain at least in part by applying a spatiotemporal filter to the subsequent acoustic signal.

In some embodiments, the subsequent acoustic signal is received in response to performing beam-steering of an acoustic beam in the region of the brain.

In some embodiments, applying the spatiotemporal filter comprises applying the spatiotemporal filter on a plurality of B-mode images generated from the subsequent acoustic signal. In some embodiments, the spatiotemporal filter is tuned to reject at least some signals of the subsequent acoustic signal.

In some embodiments, applying the spatiotemporal filter comprises extracting the measure of brain tissue motion using singular value decomposition from a plurality of images generated from the subsequent acoustic signal.

In some embodiments, the method further comprises transmitting the acoustic signal to the at least one region of the brain. In some embodiments, the subsequent acoustic signal comprises a reflection of the acoustic signal.

In some embodiments, the method further comprises determining a measure of intracranial pressure and/or a measure of intracranial elastance based on the measure of brain tissue motion.

According to some aspects, there is provided a method for determining a measure of brain tissue motion in a brain, comprising: receiving a subsequent acoustic signal from at least one region of the brain; and determining the measure of brain tissue motion in the at least one region of the brain at least in part by filtering the subsequent acoustic signal, wherein filtering the subsequent acoustic signal comprises decomposing the subsequent acoustic signal into a plurality of component signals (e.g., using kernel principal component analysis, blind source separation, etc.).

In some embodiments, the method further comprises transmitting the acoustic signal to the at least one region of the brain. In some embodiments, the subsequent acoustic signal comprises a reflection of the acoustic signal.

In some embodiments, the method further comprises determining a measure of intracranial pressure and/or a measure of intracranial elastance based on the measure of brain tissue motion.

According to some aspects, there is provided a method for determining a measure of brain tissue motion in a brain, comprising: receiving a subsequent acoustic signal from the at least one region of the brain; and determining the measure of brain tissue motion in the at least one region of the brain at least in part by tracking a feature of the brain tissue over a period of time based on a plurality of images and/or measurements generated from the subsequent acoustic signal.

In some embodiments, tracking the feature of the brain tissue over the period of time comprises determining a measure of similarity between consecutive images of the plurality of images. In some embodiments, the feature comprises a distance between two points in the brain tissue, a surface area of the brain tissue, and/or a volume of the brain tissue.

In some embodiments, the method further comprises transmitting the acoustic signal to the at least one region of the brain. In some embodiments, the subsequent acoustic signal comprises a reflection of the acoustic signal.

In some embodiments, the method further comprises determining a measure of intracranial pressure and/or a measure of intracranial elastance based on the measure of brain tissue motion.

According to some aspects, there is provided a method for determining a measure of brain tissue motion in a brain, comprising: receiving a subsequent acoustic signal from the at least one region of the brain; and determining the measure of brain tissue motion in the at least one region of the brain at least in part by filtering the subsequent acoustic signal, wherein filtering the subsequent acoustic signal comprises: generating a plurality of images from the subsequent acoustic signal; based on a first image of the plurality of images, grouping pixels at different spatial locations in the first image into a first group of pixels; and determining an average temporal signal of the group of pixels across the plurality of images. In some embodiments, the different spatial locations do not neighbor each other.

In some embodiments, the method further comprises transmitting the acoustic signal to the at least one region of the brain. In some embodiments, the subsequent acoustic signal comprises a reflection of the acoustic signal.

In some embodiments, the method further comprises determining a measure of intracranial pressure and/or a measure of intracranial elastance based on the measure of brain tissue motion.

The aspects and embodiments described above, as well as additional aspects and embodiments, are described further below. These aspects and/or embodiments may be used individually, all together, or in any combination, as the application is not limited in this respect.

II. Biology of the Brain

As described herein, aspects of the technology described herein relate to techniques for measuring motion and pulsatility in the brain, and in particular, in brain tissue. The brain tissue compartment comprises the cells (neurons and glia) as well as the interstitial fluid, with intertwined behaviors, much like compartments of an engine. The brain's power lines are a vast, fractal web of arteries, veins, and capillaries that shuttle blood throughout the tissue, dynamically routing energy to more active regions. There is a wealth of information contained in the blood flow and mechanics of brain tissue. Accurate measurements of the associated metrics of blood flow and brain tissue mechanics may enable transformative medical applications such as monitoring the health of the brain tissue, predicting seizures, and diagnosing diseases that affect the blood vessels, including strokes, as well as acute conditions like brain swelling that, if not caught, can lead to death.

Generally all adverse conditions of the brain, such as strokes, infections, and aneurysms, produce the same effect in the brain: swelling. Therefore, when doctors wish to rule in or rule out an abnormality, they seek a few predictive metrics of brain health: intracranial pressure (ICP), Cerebral Blood Flow (CBF), and Intracranial Elastance (ICE).

a. Brain Pulsatility

The human brain is a soft and complex material that is in constant motion due to underlying physiological dynamics. During each beating of the heart, periodic variations in arterial blood pressure (ABP) are transmitted along the vasculatures of the brain resulting in subtle and relatively localized deformation and motion of brain tissue. The maintenance of adequate blood flow to the brain (cerebral blood flow) is critical for normal brain function.

Cerebral blood flow is not steady, however. The systolic increase in arterial blood pressure over the cardiac cycle causes regular variations in blood flow into and throughout the brain that are synchronous with the heartbeat. Because the brain is contained within the fixed skull, these pulsations in flow and pressure are in turn transferred into brain tissue and all of the fluids contained therein, including cerebrospinal fluid (CSF). This phenomenon is called brain pulsatility (or brain tissue motion).

The cranium, on a high level, consists of three major compartments: brain tissue, blood, and cerebral fluid. This pulsatility exists in all three compartments. Brain motion may be an important indicator when monitoring certain diseases, such as hydrocephalus and traumatic brain injury, where large changes in intracranial pressure and in the biomechanical properties of the brain can lead to significant changes in pressure and flow pulsatility. The inventors have recognized that there is a lack of ability to accurately and efficiently measure pulsatility in brain tissue, particularly using non-invasive methods.

b. Acoustoelasticity of the Brain

Brain tissue is a soft matter with the so-called hyperelastic incompressible material behavior. In other words, brain tissue can experience large reversible deformation (or strain) while maintaining the total volume constant. Inside the brain, the relationship between CSF and intracranial blood volumes is described by the Monroe Kellie doctrine. The Monroe Kellie doctrine states that because the brain is incompressible, when the skull is intact, the sum of the volumes of brain, CSF, and intracranial blood is constant. Incompressibility leads to the build-up of the background steady stress or pressure inside the brain.

Changes in intracranial pressure low frequency acts as a steady stress which affects the based acoustic properties of the brain or skull. The acoustoelastic effect is how the sound velocities (both longitudinal and shear wave velocities) of an elastic material change if subjected to an initial static stress field. This is a non-linear effect of the constitutive relation between mechanical stress and finite strain in a material of continuous mass. In classical linear elasticity theory, small deformations of most elastic materials can be described by a linear relation between the applied stress and the resulting strain. This relationship is commonly known as the generalized Hooke's law. The linear elastic theory involves second order elastic constants (known as Lame parameters) and yields constant longitudinal and shear sound velocities in an elastic material, not affected by an applied stress.

The acoustoelastic effect on the other hand includes higher order expansion of the constitutive relation (non-linear elasticity theory) between the applied stress and resulting strain, which yields longitudinal and shear sound velocities dependent on the stress state of the material. In the limit of an unstressed material the sound velocities of the linear elastic theory are reproduced.

c. Intracranial Pressure

Intracranial pressure (ICP) is defined as the pressure inside the skull (or the intracranial space), and therefore, the pressure inside the brain tissue and the cerebrospinal fluid (CSF). Normal ICP is usually considered to be 5-15 mmHg in a healthy supine adult, 3-7 mmHg in children, and 1.5-6 mmHg in infants. ICP greater than 20 mmHg is considered to be elevated. Elevated ICP is considered an important cause of secondary injury leading to irreversible brain injury and death.

ICP monitoring is used in a number of conditions, including traumatic brain injury, intracerebral hemorrhage, subarachnoid hemorrhage, hydrocephalus, malignant infarction, cerebral edema, CNS infections, and hepatic encephalopathy among others. In each of these conditions, ICP monitoring in the light of other parameters can influence management for better outcomes. There are several conditions where it is important to monitor ICP, as even minor fluctuations may require a change in management.

Existing techniques for monitoring ICP predominantly include an intraventricular catheter connected to an external pressure transducer. The catheter is placed into one of the ventricles through a burr hole. The catheter can also be used for therapeutic CSF drainage and for administration of drugs. Even though it remains an accurate and cost-effective method of ICP monitoring, use of an intraventricular catheter is associated with a number of complications. These include risk of infection, hemorrhage, obstruction, difficulty in placement, malposition, etc. Other invasive modalities for ICP monitoring include intraparenchymal monitors, subdural, and epidural devices, as well as lumbar puncture measurements. Each of these modalities entail the same complications as intraventricular catheter insertion.

As described herein, complications of invasive ICP monitoring techniques include disconnection, device failure, infection, and hemorrhage. Ventricular-catheter related infection rates are around 10% and are associated with the duration of catheter placement. Clinically symptomatic hemorrhages due to the catheter range from 0.7% to 2.4%.

Transcranial ultrasound/doppler is currently widely used in neurocritical care. The status quo for transcranial ultrasound either relies on an existing high-end ultrasound scanner or a dedicated transcranial doppler (TCD) system. TCD devices are noninvasive bedside equipment used for measuring cerebral vasculature and blood flow velocity in the brain's blood vessels or flow velocity in intracranial arteries. They are used for diagnostic as well as continuous monitoring purposes. TCD devices are used for diagnosis of conditions and diseases such as stenosis, emboli, hemorrhage, sickle cell disease, ischemic cerebrovascular disease, and cerebral circulatory arrest. High end ultrasound scanners usually are limited in the frame rate, bulky, and expensive. TCD systems, at their core, are limited to only measuring blood velocity in the vasculature at the base of the brain and predominantly use a single-element transducer technology (without beam-steering capability). As such, their performance has a high level of uncertainty and questionable accuracy, as the location and angle with respect to the vessels are difficult to determine accurately. None of the technologies above are easy-to-use. That is, the operator must first be trained on how to place the probe and identify the right location of the vessels around the Circle of Willis. For continuous monitoring, dedicated TCD systems often provide a robotic arm and headset that can automatically adjust the probe (mechanically) to assure a good quality signal. However, this feature comes at a high selling price.

d. Brain Anatomy, Mechanics, and Hemodynamics

The brain is composed of the cerebrum, cerebellum, and brainstem. The cerebrum is the largest part of the brain and is composed of right and left hemispheres. It performs higher functions like interpreting touch, vision and hearing, as well as speech, reasoning, emotions, learning, and fine control of movement. The cerebellum is located under the cerebrum. Its function is to coordinate muscle movements, maintain posture, and balance. The brainstem acts as a relay center connecting the cerebrum and cerebellum to the spinal cord. It performs many automatic functions such as breathing, heart rate, body temperature, wake and sleep cycles, digestion, sneezing, coughing, vomiting, and swallowing.

Figure 1B:
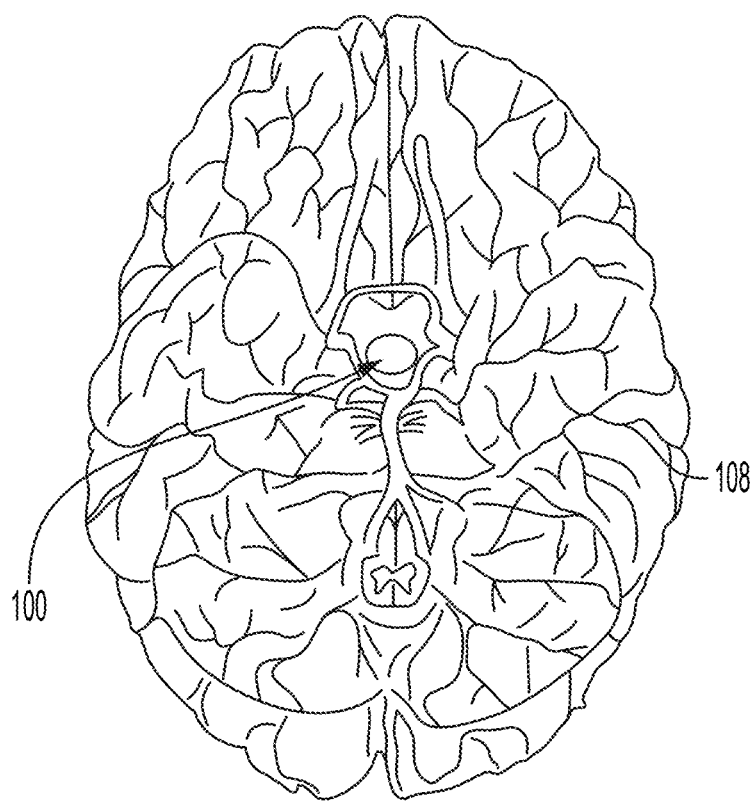
Figure 1C:
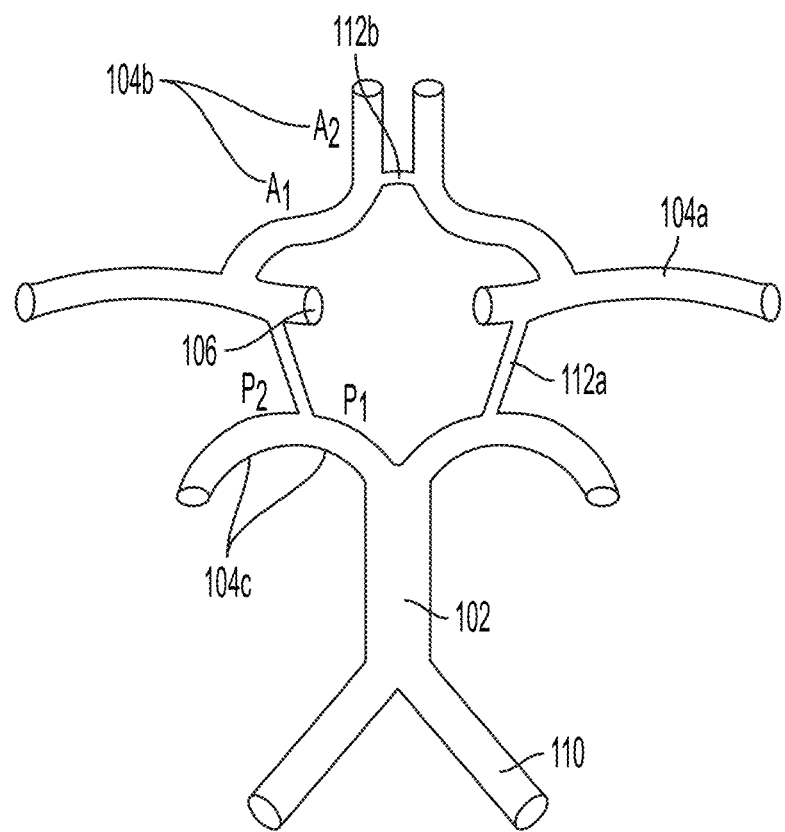

The Circle of Willis is a collection of arteries at the base of the brain. FIGS. 1A-1C show the Circle of Willis 100 and its location in the brain 108. The arteries included in the Circle of Willis 100 comprise the basilar artery 102, the middle, anterior, and posterior cerebral arteries 104a-c, the internal carotid artery 106, the vertebral artery 110, and the posterior and anterior communicating arteries 112a-b.

The Circle of Willis provides the blood supply to the brain. In general terms, the Circle of Willis connects two arterial sources together to form the arterial circle shown in FIGS. 1A-1C, which then supplies oxygenated blood to over 80% of the cerebrum. The structure encircles the middle area of the brain, including the stalk of the pituitary gland and other important structures. The two carotid arteries 106 supply blood to the brain through the neck and lead directly to the Circle of Willis. Each carotid artery branches into an internal and external carotid artery. The internal carotid artery then branches into the cerebral arteries 104a-c. This structure allows all of the blood from the two internal carotid arteries to pass through the Circle of Willis. The internal carotid arteries branch off from here into smaller arteries, which deliver much of the brain's blood supply.

Figure 2:
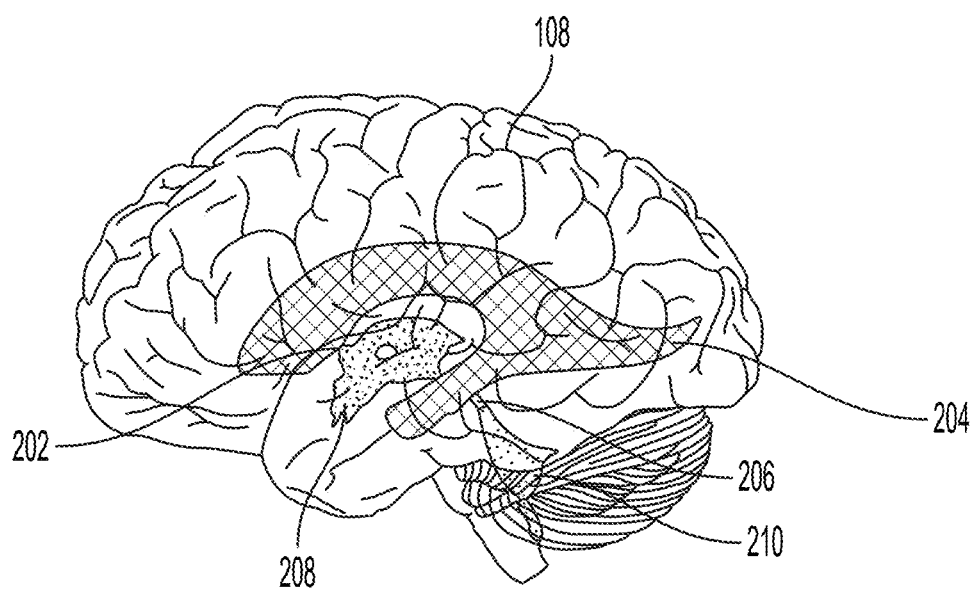
FIG. 2 shows an overview of brain ventricles.

FIG. 2 shows an overview of brain ventricles. The brain ventricles are four internal cavities that contain cerebrospinal fluid (CSF). Ventricles are critically important to the normal functioning of the central nervous system. Infection (such as meningitis), bleeding or blockage can change the characteristics of the CSF. Brain ventricles' shape can be very useful in diagnosing various conditions such as intraventricular hemorrhage and intracranial hypertension. CSF flows within and around the brain and spinal cord to help cushion it from injury. This circulating fluid is constantly being absorbed and replenished. There are two ventricles deep within the cerebral hemispheres called the lateral ventricles 204. They both connect with the third ventricle 208 through a separate opening called the Foramen of Monro 202. The third ventricle 208 connects with the fourth ventricle 210 through a long narrow tube called the aqueduct of Sylvius 206. From the fourth ventricle 210, CSF flows into the subarachnoid space where it bathes and cushions the brain 108. CSF is recycled (or absorbed) by special structures in the superior sagittal sinus called arachnoid villi. A balance is maintained between the amount of CSF that is absorbed and the amount that is produced. A disruption or blockage in the system can cause a buildup of CSF, which can cause enlargement of the ventricles (hydrocephalus) or cause a collection of fluid in the spinal cord (syringomyelia).

Figure 3:
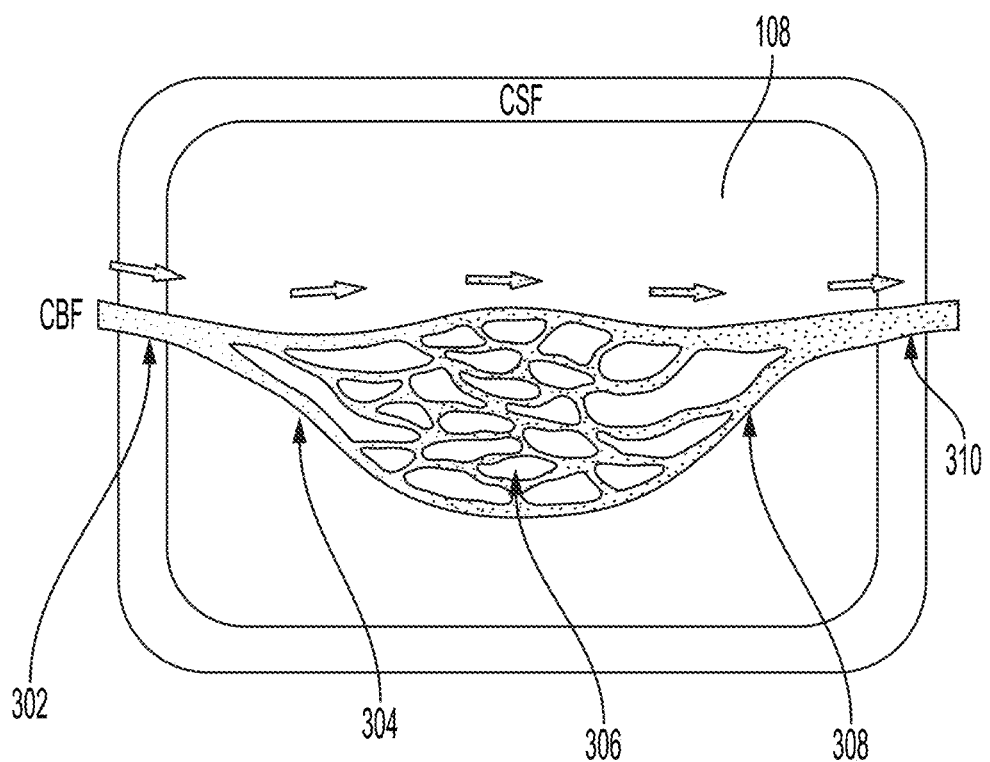
FIG. 3 shows a hemodynamic model of the brain.

FIG. 3 shows a hemodynamic model of the brain. As shown in FIG. 3, CBF moves through the arteries 302, the arterioles 304, the capillaries 306, the venules 308, and the veins 310. Brain tissue surrounds the CBF and CSF surrounds the brain.

III. Device Overview a. Sensing Mechanisms

In some embodiments, pulsatility mode sensing may be facilitated using a device which performs acoustic sensing. Acoustic, sound, or ultrasound as used herein may refer to any physical process that involves propagation of mechanical waves, including ultrasound and elastic waves. Accordingly, acoustic waves may include ultrasound waves. In some embodiments, pulsatility mode sensing is performed via ultrasonic transducers either by a single transducer or by a plurality of transducers (e.g., in pairs) to send and receive sound waves into/from the brain. A transducer is a device that converts electrical to mechanical energy and vice versa, and which can therefore send and receive ultrasound or acoustic waves. A pulsatility mode measurement may be conducted by pulsing a transducer and measuring (e.g., "listening to") the response from the brain either at the same or other transducers.

A subsequent acoustic wave may be received by one or more transducers. The subsequent acoustic wave may be a result of reflection of an acoustic wave transmitted by one or more transducers. In some embodiments, the subsequent acoustic wave may be a result of scattering (e.g., backscattering), a second order reflection or scattering, and/or absorption of acoustic/ultrasound waves in tissue.

Figure 4:
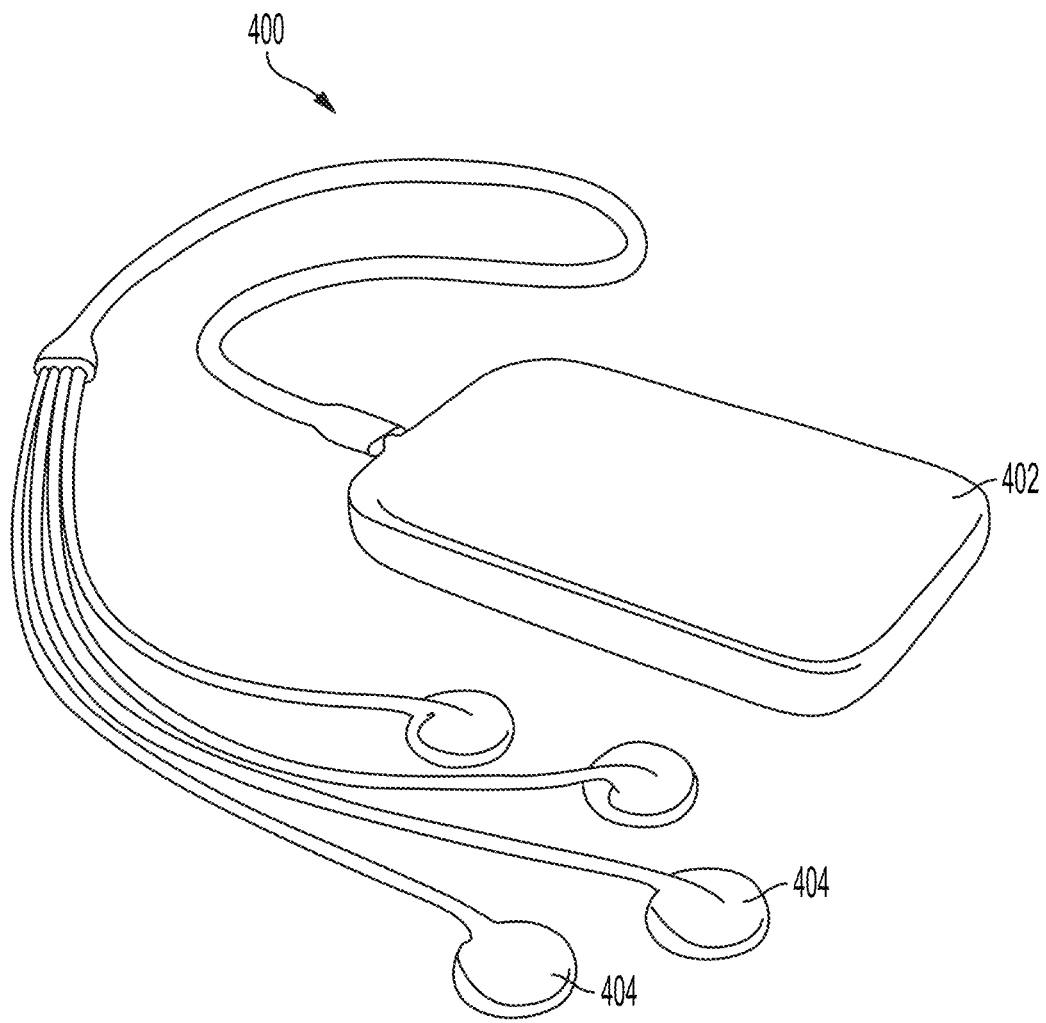
FIG. 4 shows an illustrative device for measuring brain tissue motion in the brain, according to some embodiments.
Figure 5:
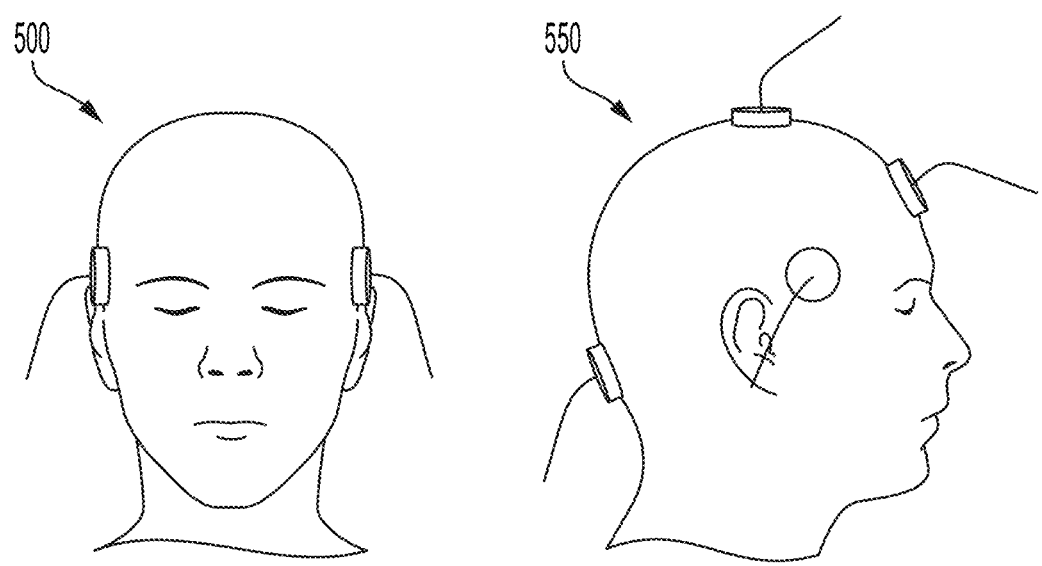
FIG. 5 shows illustrative arrangements of multiple probes of the device of FIG. 4 over a patient's head, according to some embodiments.

FIG. 4 shows an illustrative device 450 for measuring pulsatility in the brain, according to some embodiments. The device 450 may include a hub 452 and multiple probes 454 to access different brain compartments from various points over the head. FIG. 5 shows illustrative arrangements of multiple probes of the device of FIG. 4 over a patient's head, according to some embodiments. For example, in arrangement 500, two probes are placed on the patient's head to access appropriate brain compartments. In another example, in arrangement 550, fives probes are placed around the patient's head to get better access to different compartments of the brain of the person as compared to arrangement 500. The hub may communicate wirelessly with an App or software and/or a cloud platform. The hardware and transducers (or probes) may be designed in a scalable way for future launches of the product or releases of the software, to add new features such as improved algorithms or more sophisticated modes of measurements.

Figure 6:
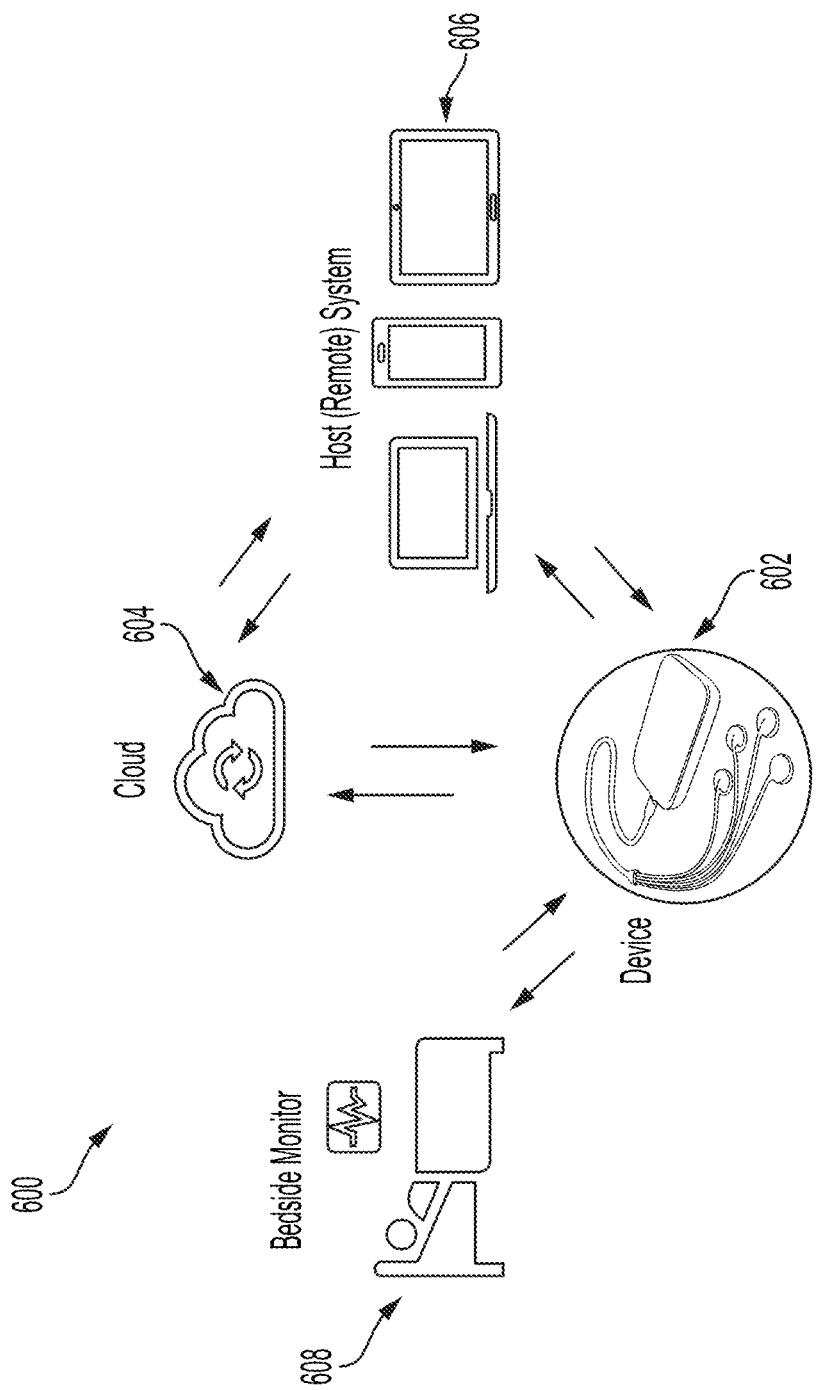
FIG. 6 shows illustrative system connectivity for the device of FIG. 4, according to some embodiments.

FIG. 6 shows illustrative system connectivity for the device of FIG. 4, according to some embodiments. In block diagram 600, device 602 can be compact and portable/wearable and can continuously stream data to a cloud platform 604 for doctors to view and analyze, equipped with an App or software 606 (on a cell phone, tablet, or a computer) for viewing data and analysis for patient 608. The device can have a wireless hub that is light, portable, and easy to charge. The hub may include a processor to perform part or all the analysis of data from the patient's head. In cases where the hub performs part of the analysis, the remaining analysis may be performed by the cloud platform 604. Such an arrangement may allow for a smaller hub design and/or require lower battery or power usage. The device can host additional sensors or probes to provide a comprehensive multimodal assessment, be synced with other instruments and/or be linked to patient monitors. For example, the device can be deployed for at the patient's bedside for remote monitoring. In another example, the device may be capable of communication with a remote system to enable telemedicine applications for analyzing the brain. The device may be capable of continuous monitoring of the brain. For example, the Device may be capable of continuous monitoring of the brain for more than six hours, for more than six hours and less than 24 hours, for more than 24 hours, and/or for another time period suitable for continuous monitoring of the brain.

Figure 7:
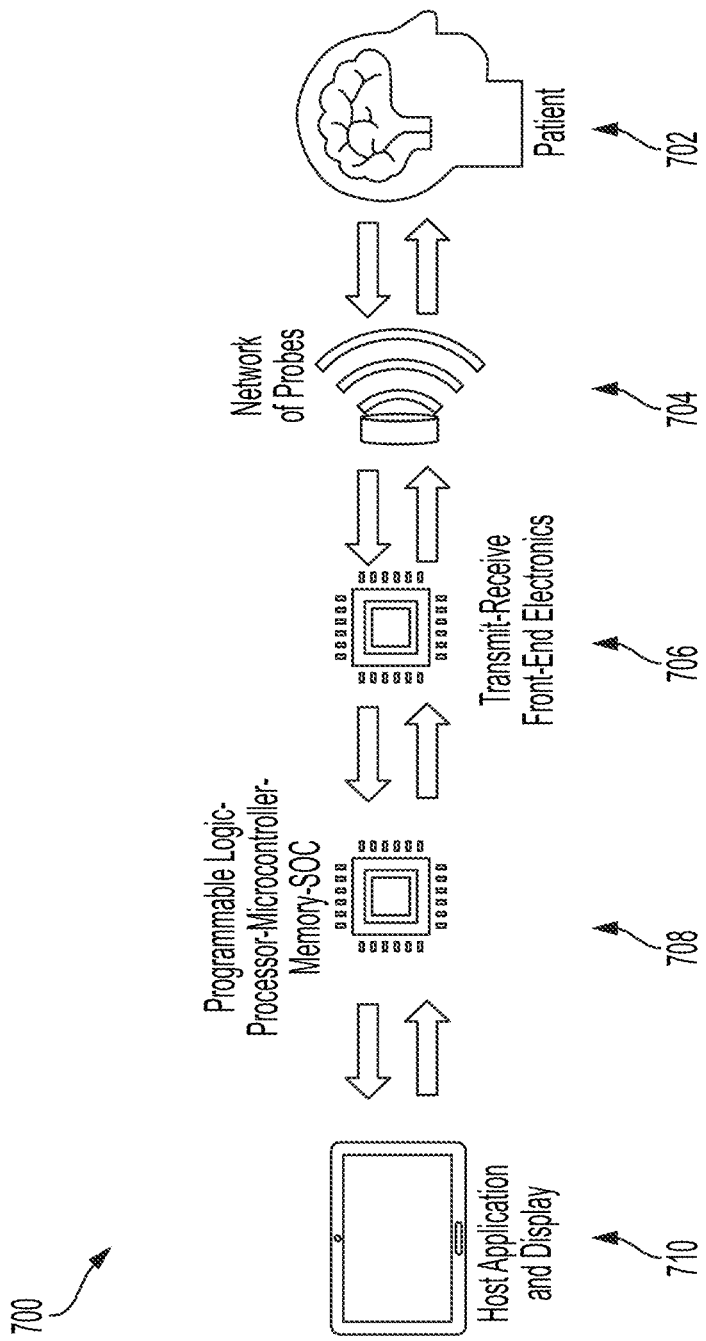
FIG. 7 shows illustrative system/hardware architecture for the device of FIG. 4, according to some embodiments.

FIG. 7 shows illustrative system/hardware architecture for the device of FIG. 4, according to some embodiments. An illustrative system/hardware architecture for a system including the device of FIG. 4 can include a network of probes for active or passive sensing of brain metrics that are connected to front-end electronics. The front-end electronics may include transmit and receive circuitry, which can include analog and mixed circuit electronics. The front-end electronics can be connected to digital blocks such as programmable logic, an FPGA, processor, and a network of memory blocks and microcontrollers to synchronize, control, and/or pipe data to other subsystems including the front-end and a host system such as a computer, tablet, smartphone, or cloud platform. Programmable logic may provide flexibility in updating the design and functionality over time by updating firmware/software without having to redesign the hardware.

In block diagram 700, patient 702 may have a network of devices 704, e.g., acoustics transducers, disposed on his or her head. The network of devices 704 may use transmit-receive electronics 706 to transmit data, e.g., e.g., wirelessly, BLUETOOTH or another suitable communication means, acquired from the brain and/or skull of patient 702. The transmit-receive electronics 706 can be connected to digital blocks such as programmable logic 708. This data may be processed and/or displayed at display 710. For example, the data may include a waveform or other suitable data received from one or more regions of the patient's brain at an APPLE WATCH or IPHONE or another suitable device that includes display 710.

Figure 8:
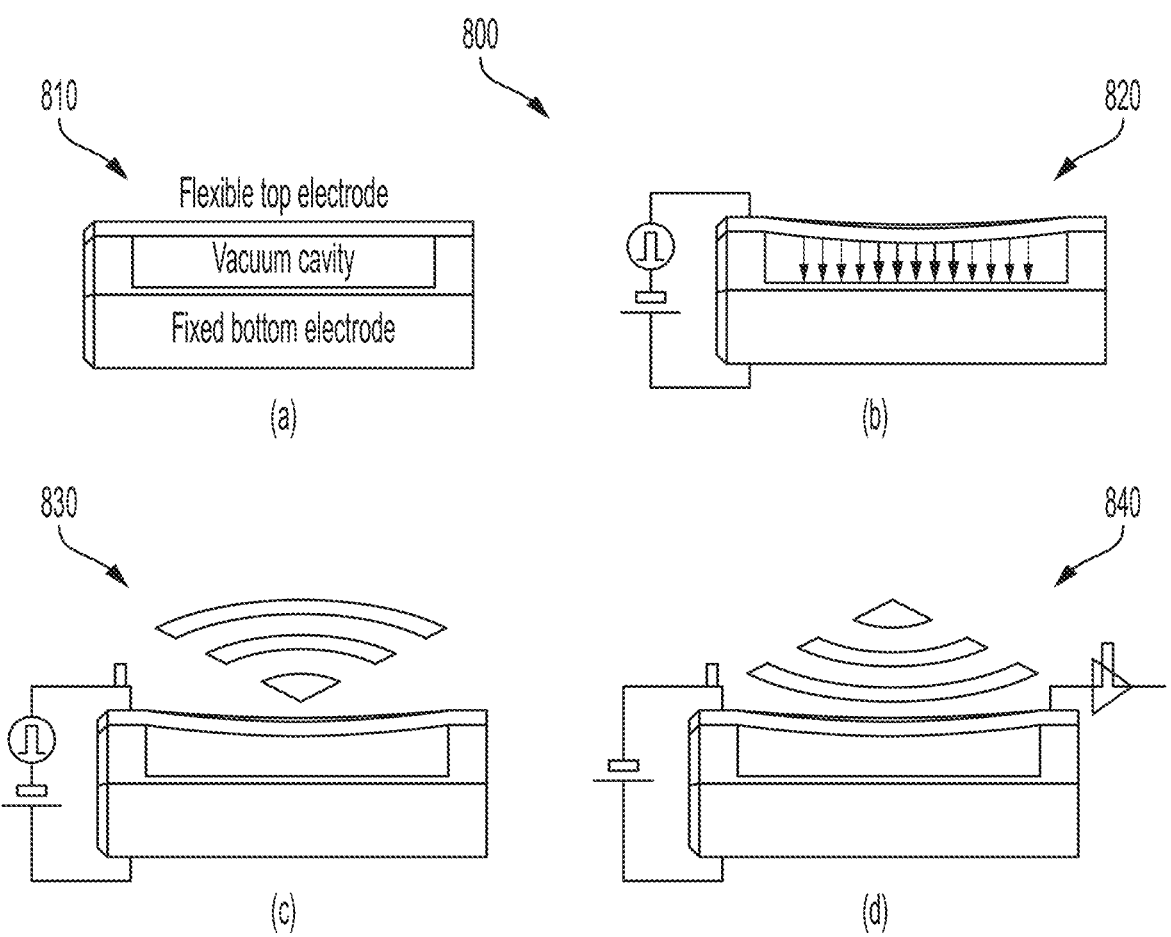
FIG. 8 shows an illustrative capacitive micromachined ultrasonic transducer (CMUT) cell, according to some embodiments.

FIG. 8 shows an illustrative capacitive micromachined ultrasonic transducer (CMUT) cell, according to some embodiments.

As described herein, pulsatility mode sensing may be facilitated by a device which includes probes that are acoustic transducers, such as piezoelectric transducers, capacitive micromachined ultrasonic transducers (CMUTs), piezoelectric micromachined ultrasonic transducer (PMUTs), electromagnetic acoustic transducers (EMATs), and other suitable acoustic transducers. Material and dimensions may determine the bandwidth and sensitivity of the transducer. In some embodiments, the device comprises one or more CMUTs. CMUTs are of particular interest as they can be easily miniaturized even at low frequencies, have superior sensitivity as well as wide bandwidth.

In some embodiments, the CMUT comprises a flexible top plate suspended over a gap, forming a variable capacitor. The displacement of the top plate creates an acoustic pressure in the medium (or vice versa; acoustic pressure in the medium displaces the flexible plate). Transduction is achieved electrostatically, by converting the displacement of the plate to an electric current through modulating the electric field in the gap, in contrast with piezoelectric transducers. The merit of the CMUT derives from having a very large electric field in the cavity of the capacitor, a field of the order of 108 V/m or higher results in an electromechanical coupling coefficient that competes with the best piezoelectric materials. The availability of microelectromechanical systems (MEMS) technologies makes it possible to realize thin vacuum gaps where such high electric fields can be established with relatively low voltages. Thus, viable devices can be realized and even integrated directly on electronic circuits such as complimentary metal-oxide-semiconductor (CMOS). FIG. 8 shows block diagram 800 including illustrations 810, 820, 830, and 840 of a CMUT cell (a) without DC bias voltage, and (b) with DC bias voltage, and principle of operation during (c) transmit and (d) receive.

In some embodiments, a further aspect is collapse mode operation of the CMUT. In this mode of operation, the CMUT cells are designed so that part of the top plate is in physical contact with the substrate, yet electrically isolated with a dielectric, during normal operation. The transmit and receive sensitivities of the CMUT are further enhanced thus providing a superior solution for ultrasound transducers. In short, the CMUT is a high electric field device, and if one can control the high electric field from issues like charging and breakdown, then one has an ultrasound transducer with superior bandwidth and sensitivity, amenable for integration with electronics, manufactured using traditional integrated circuits fabrication technologies with all its advantages, and can be made flexible for wrapping around a cylinder or even over human tissue.

One predominant example of brain motion is brain pulsatility or beating phenomena in response to one cardiac cycle, usually causing motion in the brain with a characteristic time-scale on the order of a second. Another example is neural activity such as a seizure which is expected to result from multiple action potential firings. Swelling of a single nerve fiber associated with an action potential can have a displacement of about 5 nanometers (nm) to 10 nm and a swelling pressure of about half a Pascal (Pa). The frequency of the generated displacement centers around a few kilohertz (KHz) in the acoustic range.

A pulsatility mode measurement can be conducted by a single- or many-element transducer probe. Many element transducer probes may steer acoustic or ultrasound "beams"

in the brain at different depths and directions, probing multiple locations and markers in the brain at once. The transducer probe may perform two-dimensional and three-dimensional scanning. A transducer typically consists of many transducer elements packed side-by-side one another. Each element is excited electrically by an input pulse (short or long bursts). By properly phasing (i.e., time-delaying) the pulses with respect to one another, the waves can constructively interfere in space and concentrate the wave energy in a narrow "beam" in space as the waves propagate down in tissue. This process is called transmit-beamforming. By changing the set of delays applied to the elements this beam can be steered at different directions in tissue. This process is called beam-steering. When the ultrasound beam impinges on small-scale heterogeneities (called scatterers) in tissue it is modulated by underlying motion in the tissue and scatters (reflects) backwards to the transducer. The reflected waves arrive at and are recorded by the transducer elements with different delays in time, which then synthetically are aligned and refocused in a computer to reconstruct one beam. The data may be received and a beam may be formed by collecting data at other transducer elements populated over the head. This process is called receive-beamforming. An ensemble of several beam data samples is collected and used to extract the motion of the brain using various signal processing, statistical, and ML techniques.

Pulsatility mode measurements can be used to sense changes in the brain that come from changes in functions or conditions of the brain. For example, intracranial pressure in the head appears as a small change in the mechanical properties of the brain, which manifest in the form of changes in the speed of sound or attenuation of acoustic waves. As a second example, during each beating of the heart, periodic variations in the arterial blood pressure are transmitted along the vasculatures resulting in subtle and relatively localized deformation and motion of brain tissue. Motion of brain tissue leads to modulation of the scattered waves off the heterogeneities in the tissue.

In some embodiments, pulsatility mode sensing can be used alongside other modalities such as EEG, MEG, fMRI, fNIRs, as well as functional optoacoustic/thermoacoustic imaging, to record multi-modal metrics of brain health. Applications can include but are not limited to diagnosing and monitoring traumatic brain injury, epileptic seizures, stroke, brain infection, brain aneurysm or bleeding, meningitis, end stage liver disease, septic shock, metabolic coma, or generally, any patients with altered mental status (in the field or hospital), vasospasm (VSP), brain aneurysm or bleeding, hemorrhage (intraparenchymal IPH, intraventricular IVH, subarachnoid SAH), embolism, vaso-motor reactivity (VMR), and autoregulatory mechanism, as well as evaluating collateral capacity, vasodilatory capacity, intracranial stenosis, sickle cell anemia, arteriovenous malformation, and brain death.

IV. Techniques for P-Mode Sensing

Brain tissue motion and pulsatility may be measured using various techniques, including, but not limited to, standard continuous wave doppler, or pulsed wave doppler, color doppler, or power doppler techniques, where the doppler effect due to the motion of subwavelength scatterers in brain tissue or blood is captured by measuring the shift in the carrier frequency or phase of the received waveforms. Alternatively, the numerous subwavelength scatterers present in biological tissue generate a seemingly random interferential pattern commonly referred to as "ultrasonic speckle". The motion of the subwavelength scatterers leads to changes in the speckle pattern that can be tracked in time. Thus, by tracking speckles as a function of time, one can extract the motion of brain tissue or blood cells. Various filtering techniques may be applied to extract the motion at the frequency range of interest. Aspects of these filtering techniques for measuring brain tissue pulsatility will now be discussed.

Figure 9:
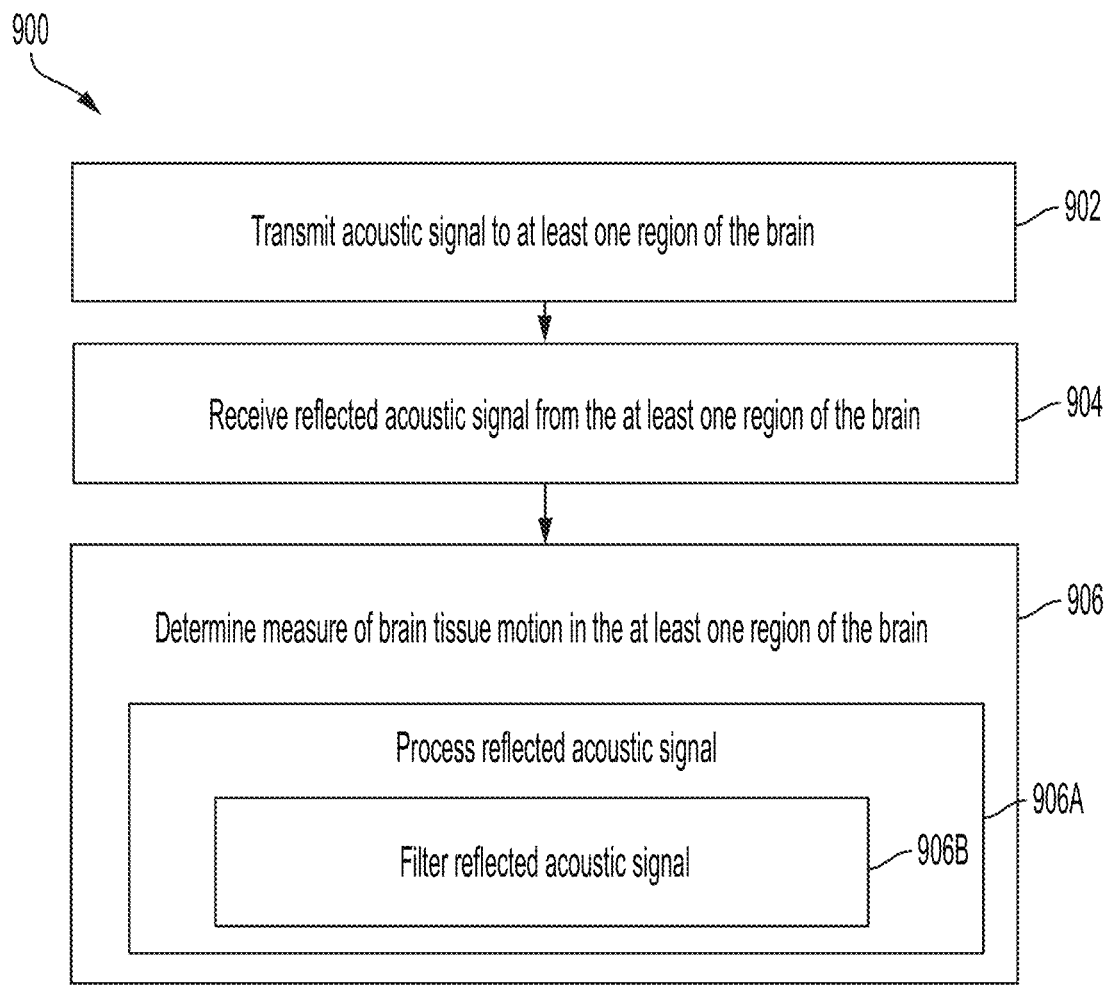
FIG. 9 shows an illustrative process for determining a measure of brain tissue motion in a brain, according to some embodiments.

FIG. 9 shows an illustrative process 900 for determining a measure of brain tissue motion in a brain, according to some embodiments. The process 900 may begin at act 902, where an acoustic signal is transmitted to at least one region of the brain. For example, as described herein, the acoustic signal may be transmitted by at least one ultrasonic transducer. In some embodiments, the acoustic signal may comprise a plurality of acoustic signals. In some embodiments, the plurality of acoustic signals may form an acoustic beam. In some embodiments, the acoustic beam may be steered to the at least one region of the brain by controlling delays of the ultrasonic transducers.

As described herein, in some embodiments, the at least one ultrasonic transducer may comprise a plurality of ultrasonic transducers. In some embodiments, the plurality of ultrasonic transducers may be arranged in an array.

At act 904, a reflected acoustic signal may be received from the at least one region of the brain. For example, the received acoustic signal may comprise a reflection of the acoustic signal transmitted at act 902. In some embodiments, the received acoustic signal may comprise at least a portion of the acoustic signal transmitted at act 902 that has either been reflected or refracted by the at least one region of the brain.

The acoustic signal may be received by at least one ultrasonic transducer. In some embodiments, the at least one ultrasonic transducer that receives the signal comprises one or more of the at least one ultrasonic transducer that transmitted the acoustic signal at act 902. In some embodiments, the at least one ultrasonic transducer that receives the signal is different than the at least one ultrasonic transducer that transmitted the acoustic signal at act 902.

At act 906, a measure of brain tissue motion in the at least one region of the brain is determined. For example, the measure of brain tissue motion may be determined based on the acoustic signal received at act 904. For example, as shown in FIG. 9, determining the measure of brain tissue motion in the at least one region of the brain may comprise processing the reflected acoustic signal at act 906A. Processing the reflected acoustic signal may comprise applying one or more techniques to filter the reflected acoustic signal at act 906B. Examples of the one or more techniques that may be applied to filter the reflected acoustic signal and determine a measure of brain tissue motion in the at least one region of the brain will now be described.

a. Spatiotemporal Filtering

Figure 10:
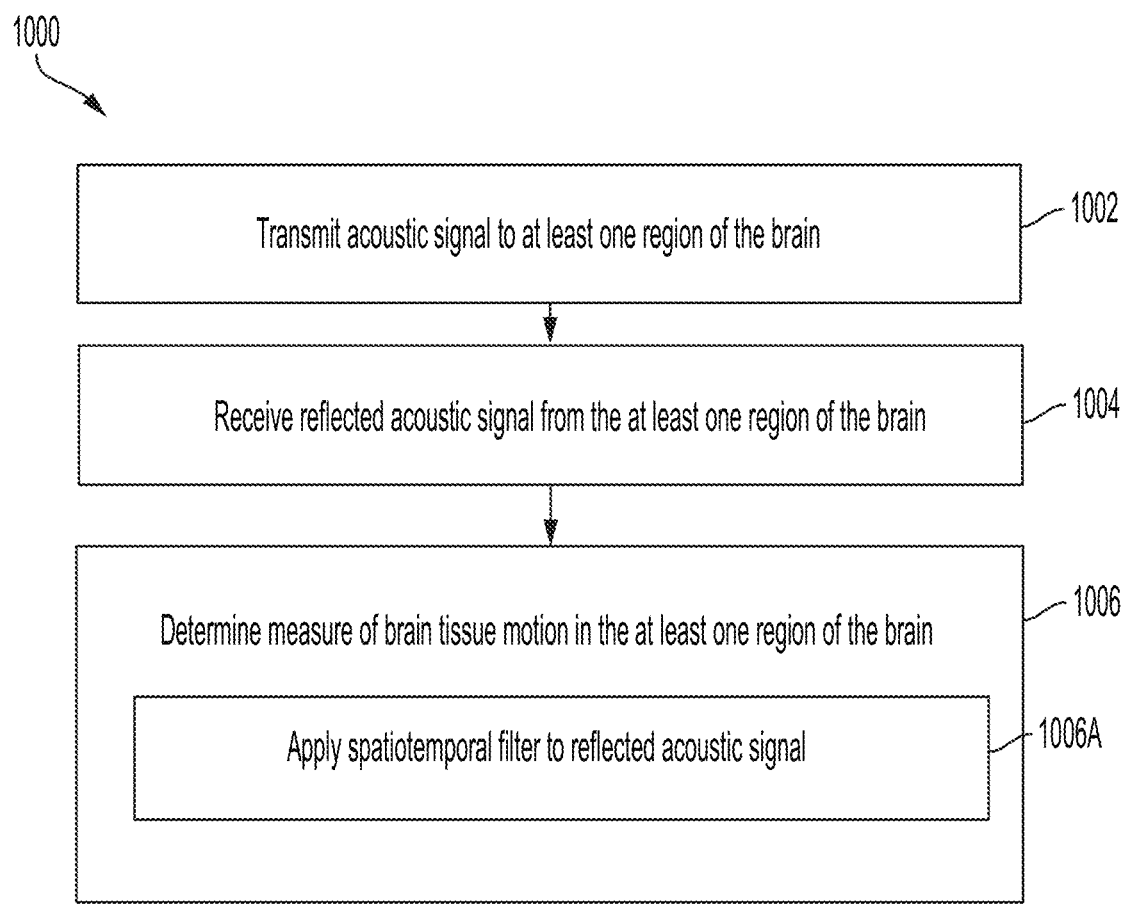
FIG. 10 shows an illustrative process for determining a measure of brain tissue motion in a brain via spatiotemporal filtering, according to some embodiments.

According to one embodiment, a spatiotemporal filtering technique may be performed to extract brain tissue motion. FIG. 10 shows an illustrative process 1000 for determining a measure of brain tissue motion in a brain via spatiotemporal filtering, according to some embodiments.

The process 1000 may begin at act 1002. Acts 1002-1006 may be performed in the same manner as acts 902-906 of process 900.

At act 1006A, the measure of brain tissue motion in the at least one region of the brain may be determined at least in part by applying a spatiotemporal filter to the reflected acoustic signal.

Figure 11:
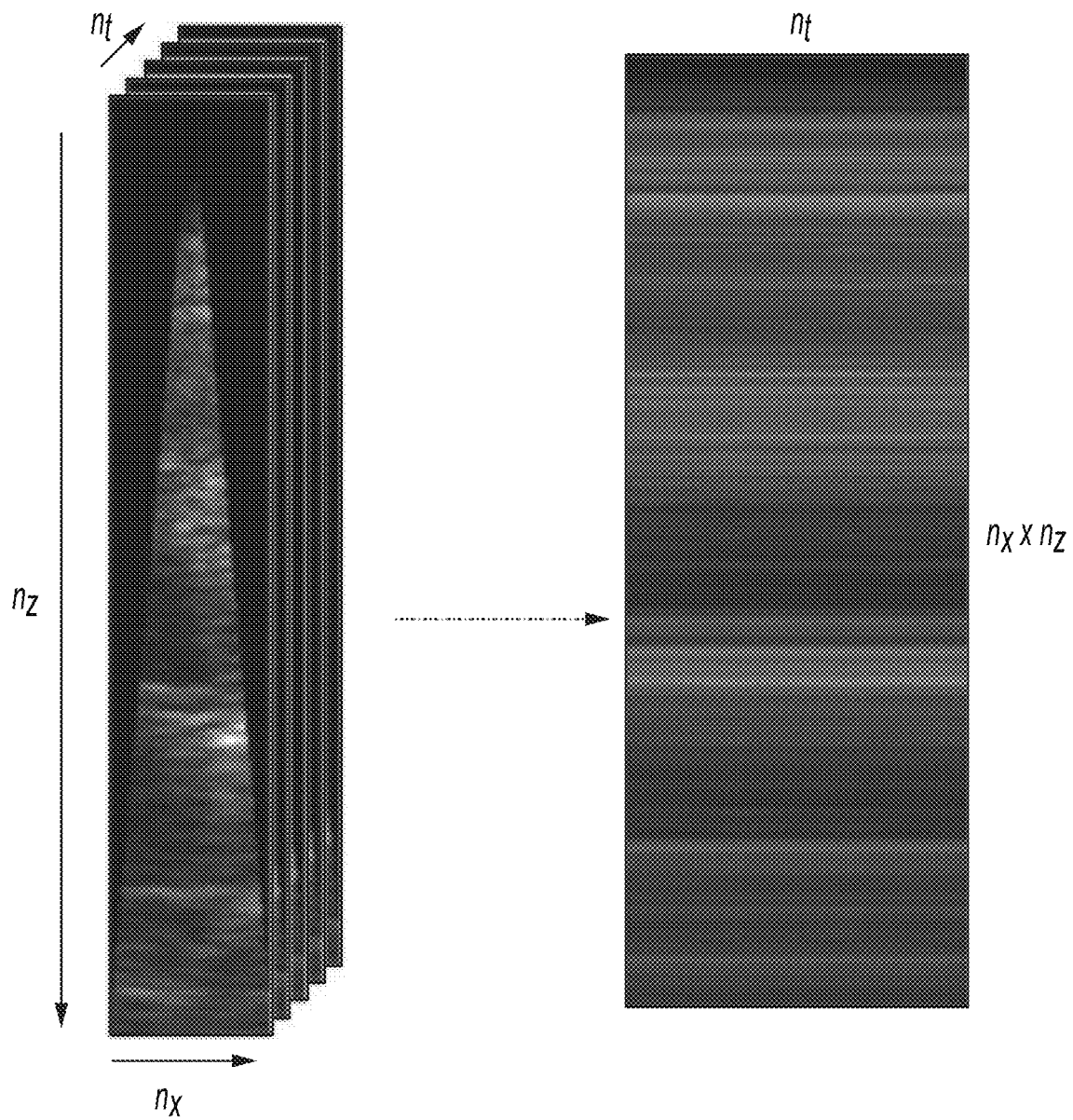
FIG. 11 shows an illustrative example of unwrapping a three-dimensional image stack into a two-dimensional matrix, according to some embodiments.

For example, the brain may be imaged using an ultrasound scanner and the brain tissue motion is extracted from a series of images using advanced spatiotemporal filtering techniques such as, but not limited to, Singular Value Decomposition (SVD), a matrix decomposition technique related to Principle Component Analysis (PCA). In this approach, an ultrasonic imaging device produces a plurality of B-mode (intensity) images of the brain. Several images of the brain may be collected at a certain frame rate, totaling a given number of seconds worth of images. The dataset thusly acquired can be seen as a three-dimensional array with spatial dimension x and z (azimuth and depth, respectively) and a temporal dimension t (time) containing $n_x \times n_z \times n_t$ values. S(x, z, t) denotes the dataset. FIG. 11 shows an illustrative example of unwrapping a three-dimensional image stack into a two-dimensional matrix, according to some embodiments. As seen in FIG. 11, the three-dimensional array containing the data can be rearranged into a two-dimensional array of size $(n_x \times n_z) \times n_t$ by unwrapping the z dimension column-wise.

S denotes this two-dimensional array. This two-dimensional matrix is suitable for SVD filtering. The first dimension of S corresponds to space whereas the second dimension is time. Performing the SVD decomposition of S amounts to finding the matrices U, Σ, and V such that:

$$S = U\Sigma V^T$$

where U is an $(n_x \cdot n_z \times n_x \cdot n_z)$ orthonormal matrix, V is an $(n_t \times n_t)$ orthonormal matrix, Σ is an $(n_x \cdot n_z \times n_t)$ diagonal, non-square matrix containing the singular values $\sigma_i$ of S:

$$\Sigma = (\sigma_1 0 \ldots 00 \ \cdot \cdot \ \vdots \ \vdots \ \cdot \ \cdot \ \vdots \ \sigma_{n_t} \vdots 0 \ \vdots \ \vdots 0 \ldots 0)$$

$V^T$ is the conjugate transpose of V. From this, it can be seen that the columns of U are the spatial vectors of S and the columns of V are the temporal singular vectors of S.

Figure 12:
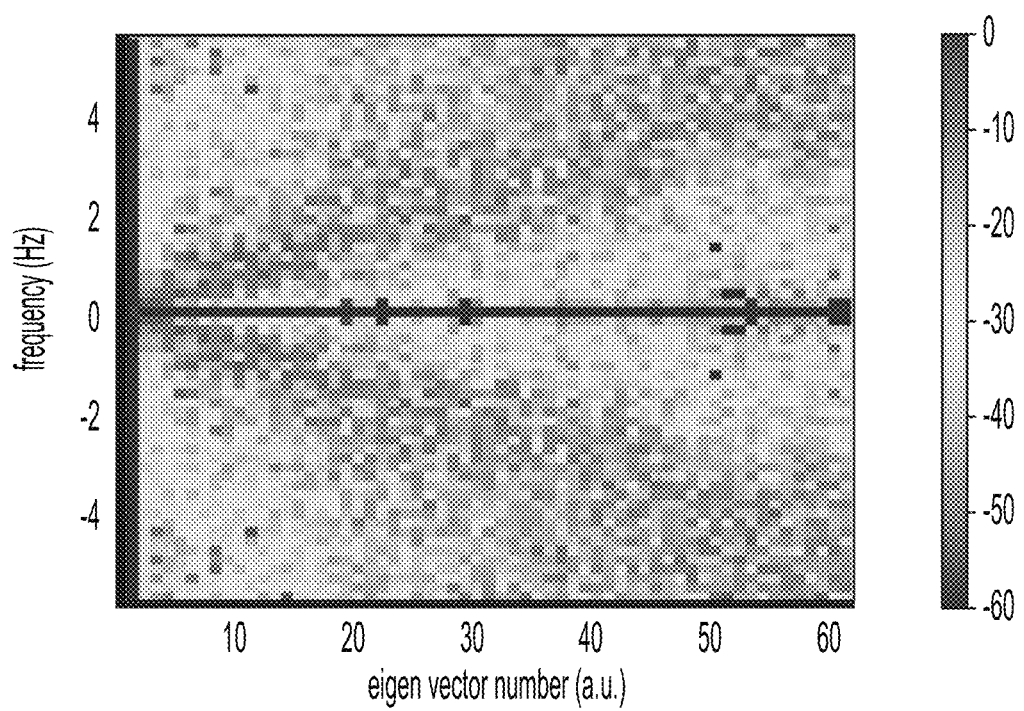
FIG. 12 shows an illustration of the power spectra of temporal singular vectors in decreasing singular value order, according to some embodiments.

FIG. 12 shows an illustration of the power spectra of temporal singular vectors in decreasing singular value order, according to some embodiments. FIG. 12 shows the spectra of the column vectors of V ordered by decreasing singular value. It can be seen that larger singular values are associated with temporal vectors V containing lower temporal frequencies, whereas smaller singular values progressively incorporate higher and higher temporal frequency content. Some of this higher frequency content is noise.

Thus, this decomposition captures the spatiotemporal variations of S in a separable form. Using this decomposition, S may be expressed as a weighted sum of the outer product of the columns of U with the columns of V:

$$S = \sum_i \sigma_i \cdot U_i \times V_i$$

The column $V_i$ describes the temporal variation associated with the corresponding spatial column $U_i$. The spatial column vector $U_i$ of size $(n_x \times n_z, 1)$, can be treated as a sub-image by $I_i$ wrapping it column-wise. It can be seen that the temporal column vector $V_i$ thus modulates the intensity of the pixels in $I_i$ in time. In other words, the intensity of all the pixels in the sub-image $I_i$ have the same temporal behavior characterized by $V_i$. As a result, spatiotemporal decomposition for each pixel of S has been achieved.

With the number of non-zero $\sigma_i$ corresponding to the rank of S, we have:

$$s(x, z, t) = \sum_{i=1}^{rank(S)} \sigma_i I_i(x, z) V_i(t)$$

The $\sigma_i$ are in decreasing order. The first and largest singular values $\sigma_i$ can be expected to be associated with static tissue since it represents the structure with the highest spatiotemporal coherence. The spatiotemporal signal associate with brain tissue emotion can be found in the other singular values, excluding the high frequency noise. Therefore, a spatiotemporal filter capable of isolating brain tissue motion simply by setting the first few singular values $\sigma_i$ of S to zero can be achieved. In other words, the filtered matrix $S_f$ can be built such that:

$$S_f = U \Sigma_f V_T$$

The matrix $\Sigma_f$ can be tuned to reject certain spatiotemporal signals and preserve others. For example, if one wants to rid the dataset from still tissue, one can set $\Sigma_f$ to be:

$$\Sigma_f = (00 \ldots 00 \sigma_2 \ \cdot \ \vdots \ \vdots \ \cdot \ \cdot \ \vdots \ \sigma_{n_t} \vdots 0 \ \vdots \ \vdots 0 \ldots 0)$$

Further, the $\sigma_i$ values may be amplified or attenuated based on the desired results. For example, in the illustrated embodiment, the $\sigma_i$ values are used to preserve brain tissue motion and reject any other spatiotemporal signal as clutter.

Figure 13:
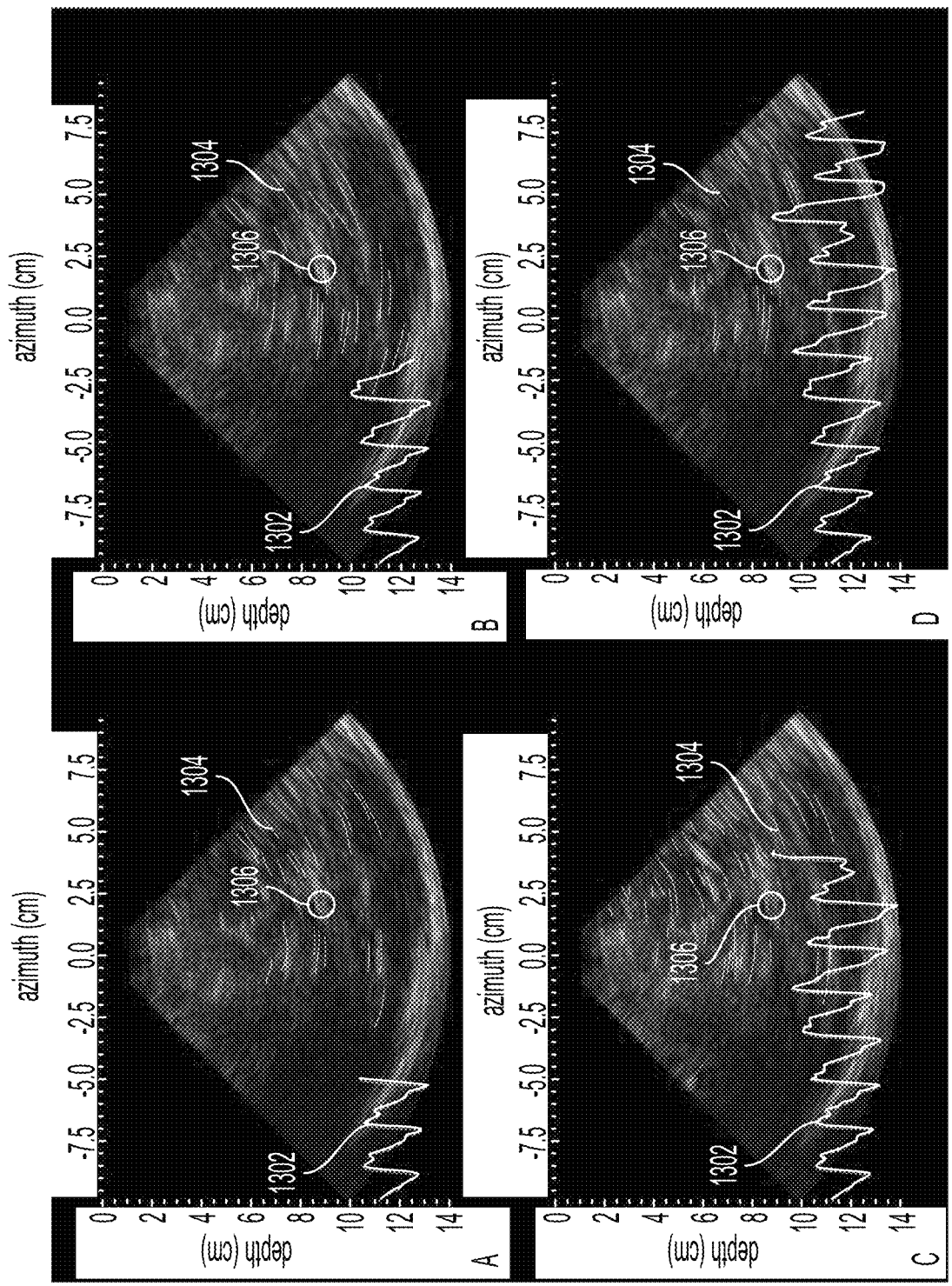
FIG. 13 shows examples of singular value decomposition filtering on a sequence of B-mode images of a patient's brain, according to some embodiments.

FIG. 13 shows examples of singular value decomposition filtering on a sequence of B-mode images of a patient's brain, according to some embodiments. FIG. 13 shows a dataset processed using the SVD filtering technique described herein. The grayscale images correspond to several ultrasound B-mode frames of a patient's brain. The overlays 1302 and inside circle 1306 shows where a beating motion is occurring in the brain. Lines 1304 indicates a decreasing pixel intensity whereas a coloration inside circle 1304 indicates increasing pixel intensity with time. The trace plotted at the bottom of each frame shows the variations of the pixel intensity in the circle 1302. Isolating the parts of the image where the brain tissue is beating with the patient's heartbeat may facilitate assessment of the stiffness of the surrounding tissue.

b. Signal Decomposition

Figure 14:
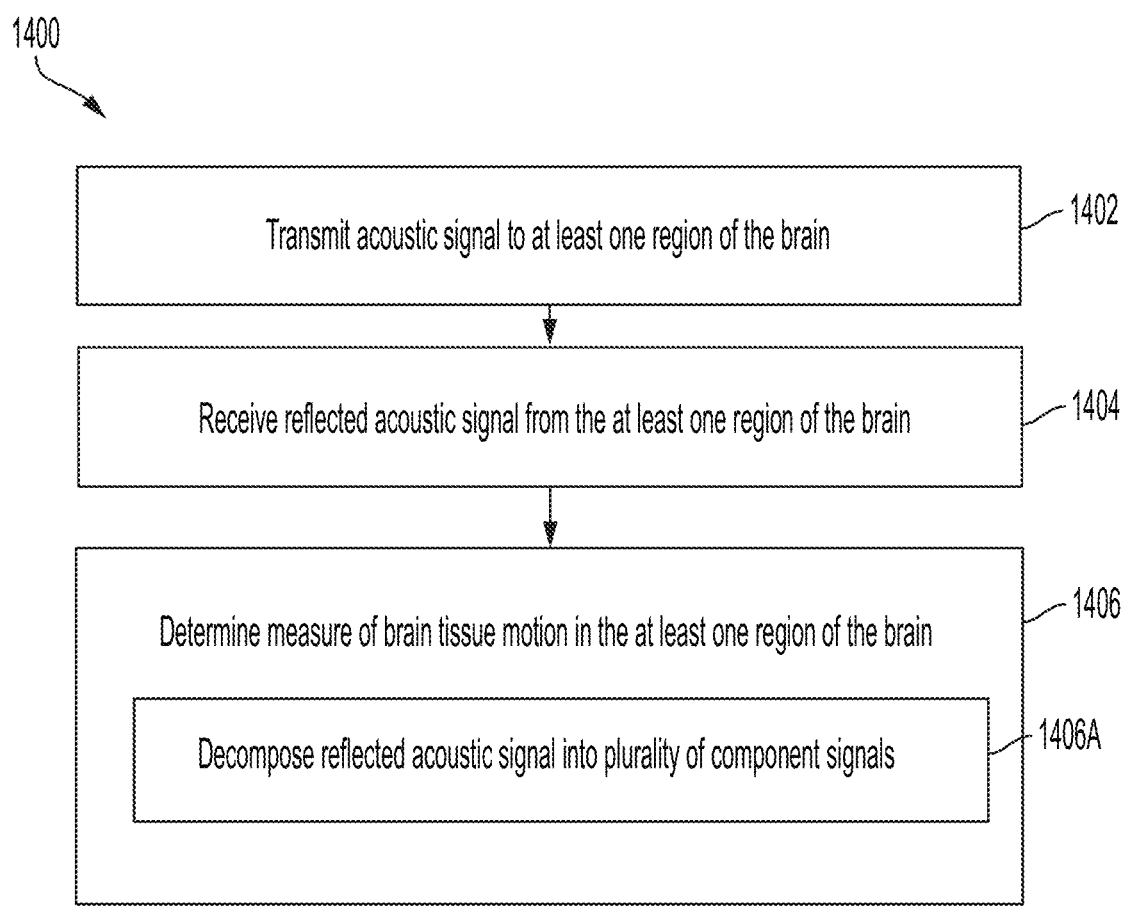
FIG. 14 shows an illustrative process for determining a measure of brain tissue motion in a brain via signal decomposition, according to some embodiments.

According to one embodiment, a signal decomposition technique may be performed to extract brain tissue motion. FIG. 14 shows an illustrative process for determining a measure of brain tissue motion in a brain via signal decomposition, according to some embodiments.

The process 1400 may begin at act 1402. Acts 1402-1406 may be performed in the same manner as acts 902-906 of process 900.

At act 1406A, the measure of brain tissue motion in the at least one region of the brain may be determined at least in part by decomposing the reflected acoustic signal into a plurality of component signals.

The goal of signal decomposition is extraction and separation of signal components from composite signals, which should preferably be related to semantic units. Examples of such signal components in composite signals are distinct objects in images or video, video shots, melody sequences in music, spoken words or sentences in speech signals. The criteria selected for separating the signals enables one to decompose a superimposed signal into components that are separable considering different aspects. For example, one example signal decomposition technique is linear discriminant analysis (LDA). LDA solves to find a subspace with an orthogonal basis in which the signals are linearly separable and the theoretical basis for many statistical signal processing algorithms holds. Other techniques may be used, such as the techniques described herein including Kernal Principal Component Analysis and Blind Source Separation, which may carry advantages over LDA. For instance, LDA assumes a linear relationship between components and measured signal, but most of the time this is not correct.

i. Kernal Principal Component Analysis (KPCA)

In some embodiments, kernel principal component analysis (KPCA) may be used to extract brain tissue motion from a set of ultrasound images. In the field of multivariate statistics, KPCA is an extension of principal component analysis (PCA) using techniques of kernel methods. Using a kernel, the originally linear operations of PCA are performed in a reproducing kernel Hilbert space. Kernel methods owe their name to the use of kernel functions, which enable them to operate in a high-dimensional, implicit feature space without ever computing the coordinates of the data in that space, but rather by computing the inner products between the images of all pairs of data in the feature space. This approach is called the "kernel trick".

Kernel functions can be non-linear but restricted by a set of constraints. For example, to extract brain tissue motion, each pixel time series may be assumed to be a measured superimposed signal in time. It may also be assumed that the components leading to these pixel time series are common among all. Accordingly, the reproducible kernel Hilbert space orthogonal basis may be solved for.

Figure 15:
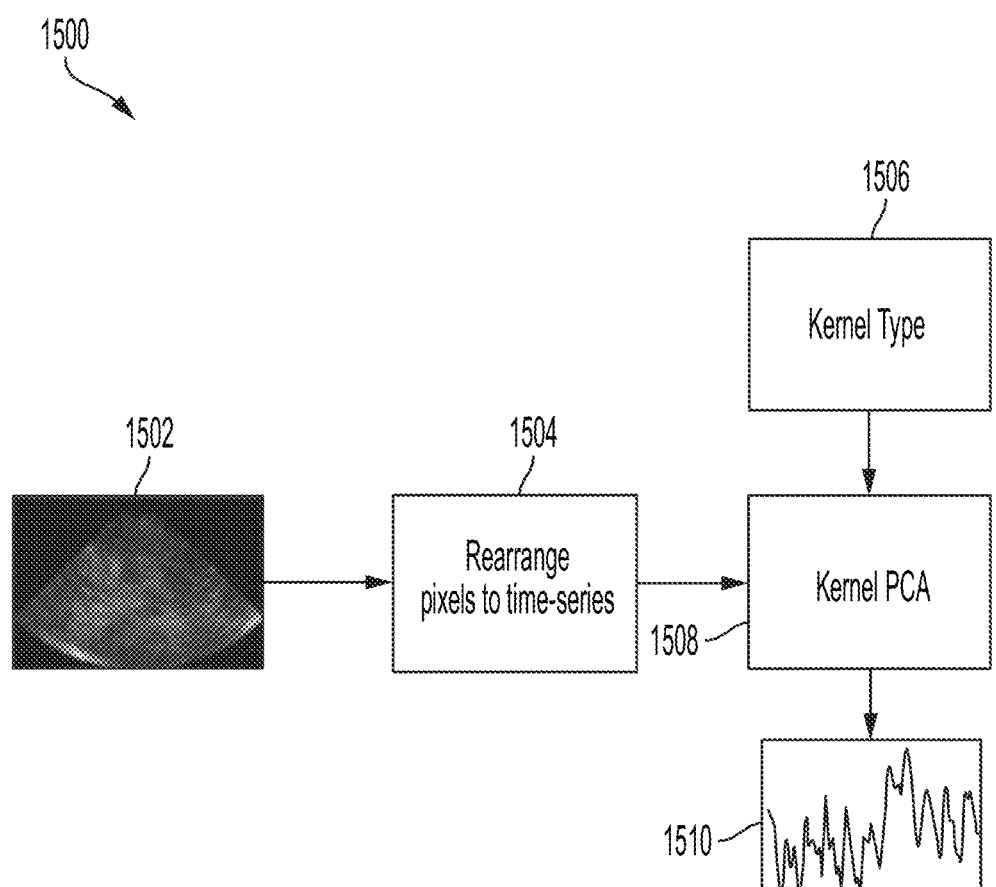
FIG. 15 shows an example flow diagram of kernel principal component analysis, according to some embodiments.

FIG. 15 shows an example flow diagram 1500 of kernel principal component analysis, according to some embodiments. The process illustrated in flow diagram 1500 may begin at act 1502 where a plurality of images are obtained. For example, the plurality of images may comprise a plurality of B-mode ultrasound images.

At act 1504, pixels in the plurality of images obtained at act 1502 may be rearranged into a time-series.

At act 1506, a kernel type may be selected for use in the signal decomposition technique. Any suitable kernel technique may be selected. For example, in some embodiments, a cosine kernel may be implemented.

At act 1508, principal component analysis may be performed using the kernel type selected at act 1506. The goal of act 1508 is to decompose the signals obtained at act 1502 to identify at least one signal representative of brain tissue motion. Plot 1510 shows an example of a signal extracted from the plurality of images using KPCA.

Figure 16:
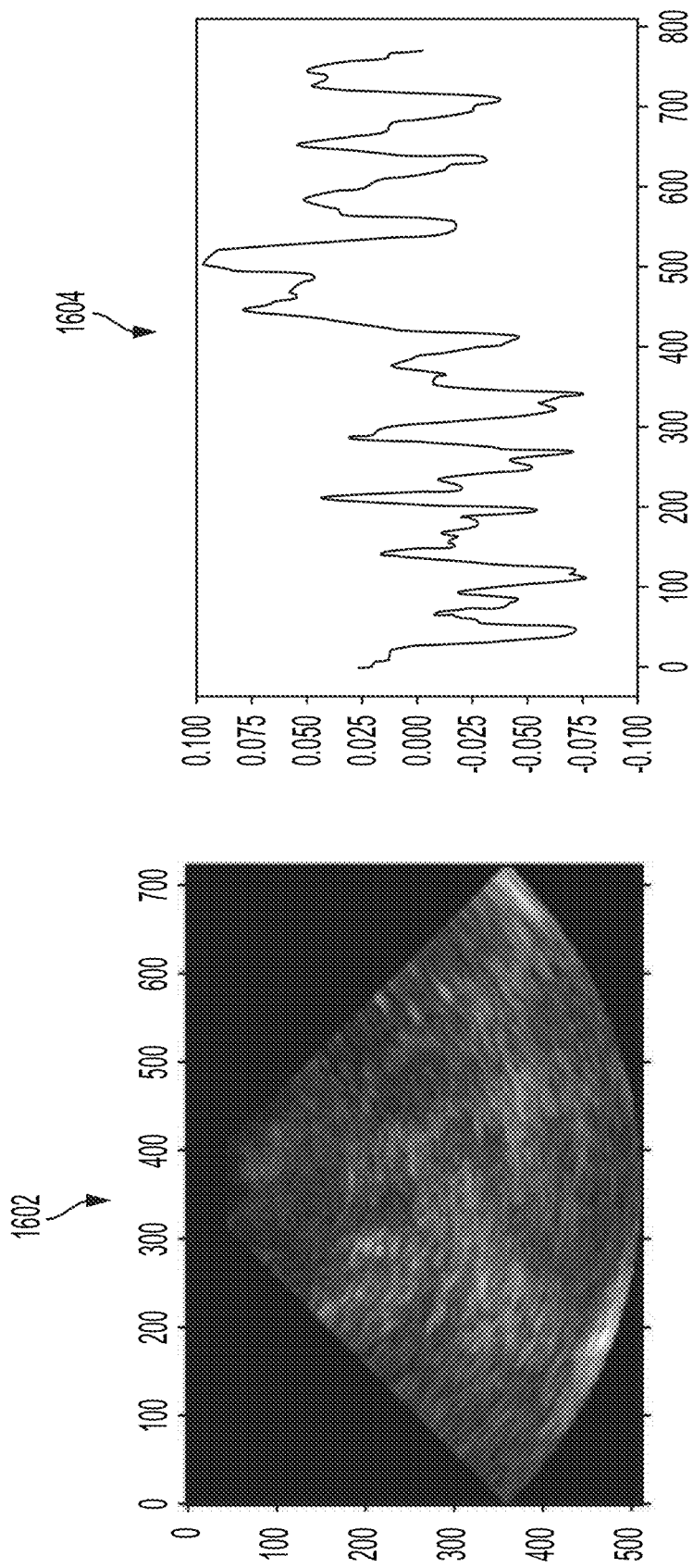
FIG. 16 shows example images of extracted components from kernel principal component analysis, according to some embodiments.

FIG. 16 shows example images of extracted components from kernel principal component analysis, according to some embodiments. In the illustrated example, a 'cosine' kernel and a time series of brightness mode images 1602 in a plane that contains brain ventricles was used. The extracted signal is presented in plot 1604.

ii. Blind Source Separation (BSS)

In some embodiments, Blind Source Separation (BSS) may be used to extract brain tissue motion from a set of ultrasound images. BSS refers to a problem where both the sources and the mixing methodology are unknown, only mixture signals are available for further separation processing. In several situations it is desirable to recover all individual sources from the mixed signal, or at least to segregate a particular source. There are various methods with different assumptions to identify underlying signal sources and/or mixing forward models e.g. common spatial patterns, stationary subspace analysis, dependent component analysis, independent component analysis (ICA) etc.

For example, in some embodiments, independent component analysis (ICA) may be implemented for separating signal sources from brightness image time-series. In signal processing, ICA is a computational method for separating a multivariate signal into additive subcomponents. This may be performed by assuming that the subcomponents are non-Gaussian signals and that they are statistically independent from each other.

Figure 17A:
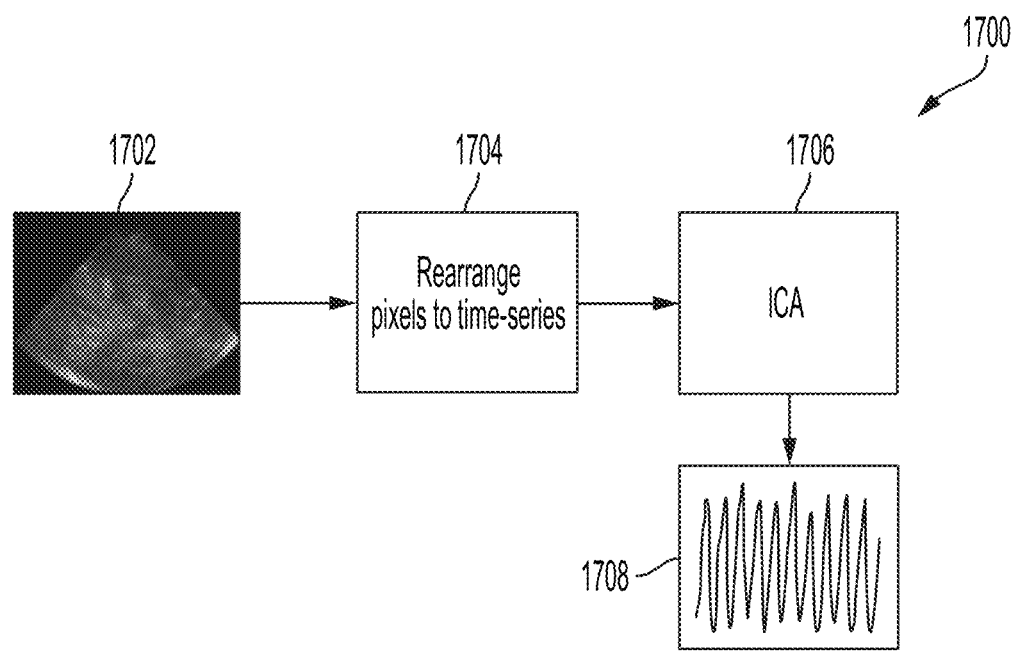
FIG. 17A shows an example flow diagram of independent component analysis, according to some embodiments.

FIG. 17A shows an example flow diagram 1700 of independent component analysis, according to some embodiments. The process illustrated in flow diagram 1700 may begin at act 1702 where a plurality of images are obtained. For example, the plurality of images may comprise a plurality of B-mode ultrasound images.

At act 1704, pixels in the plurality of images obtained at act 1702 may be rearranged into a time-series.

At act 1706, independent component analysis may be performed. The goal of act 1706 is to decompose the signals obtained at act 1702 to identify at least one signal representative of brain tissue motion. Plot 1708 shows an example of a signal extracted from the plurality of images using ICA.

Figure 17B:
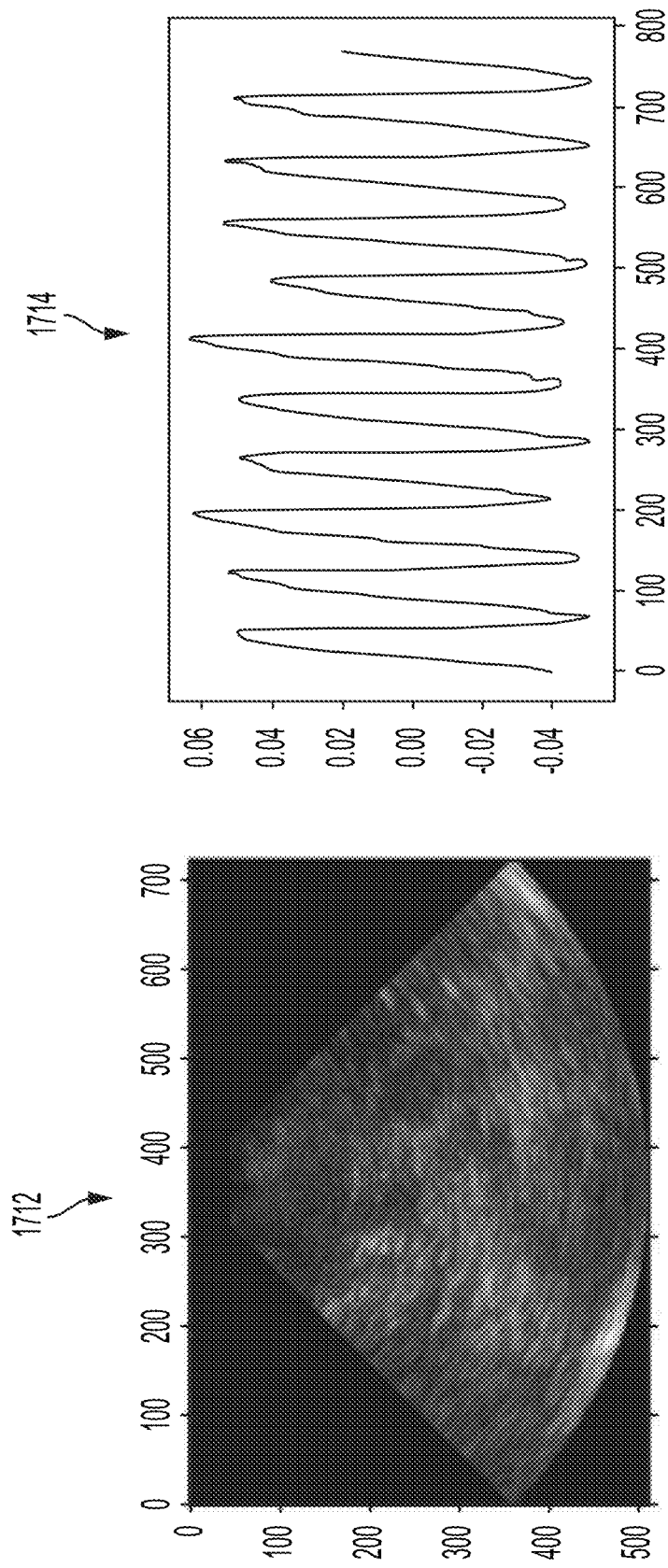
FIG. 17B shows example images of extracted components from independent component analysis, according to some embodiments.

FIG. 17B shows example images of extracted components from independent component analysis, according to some embodiments. In particular, image 1712 shows an example of a B-mode image of brain tissue obtained from a region of the brain. Plot 1714 shows an example of an extracted signal obtained via signal decomposition according to process 1700. The extracted signal may be representative of brain tissue motion in the region of the brain.

ICA is a special case of blind source separation. An example application of ICA is the "cocktail party problem" of listening in on one person's speech in a noisy room. To perform this analysis one can propose a linear forward model as the mixing function or propose other non-linear methods.

In some embodiments, one or more blind source separation techniques may be used in addition or alternative to the techniques described herein. For example, in some embodiments, non-linear ICA may be used. For example, the relationship between different beating signal waveshapes, including intracranial pressure morphology, could be non-linearly encoded in speckle's temporal statistics.

c. Tissue Tracking

Figure 18:
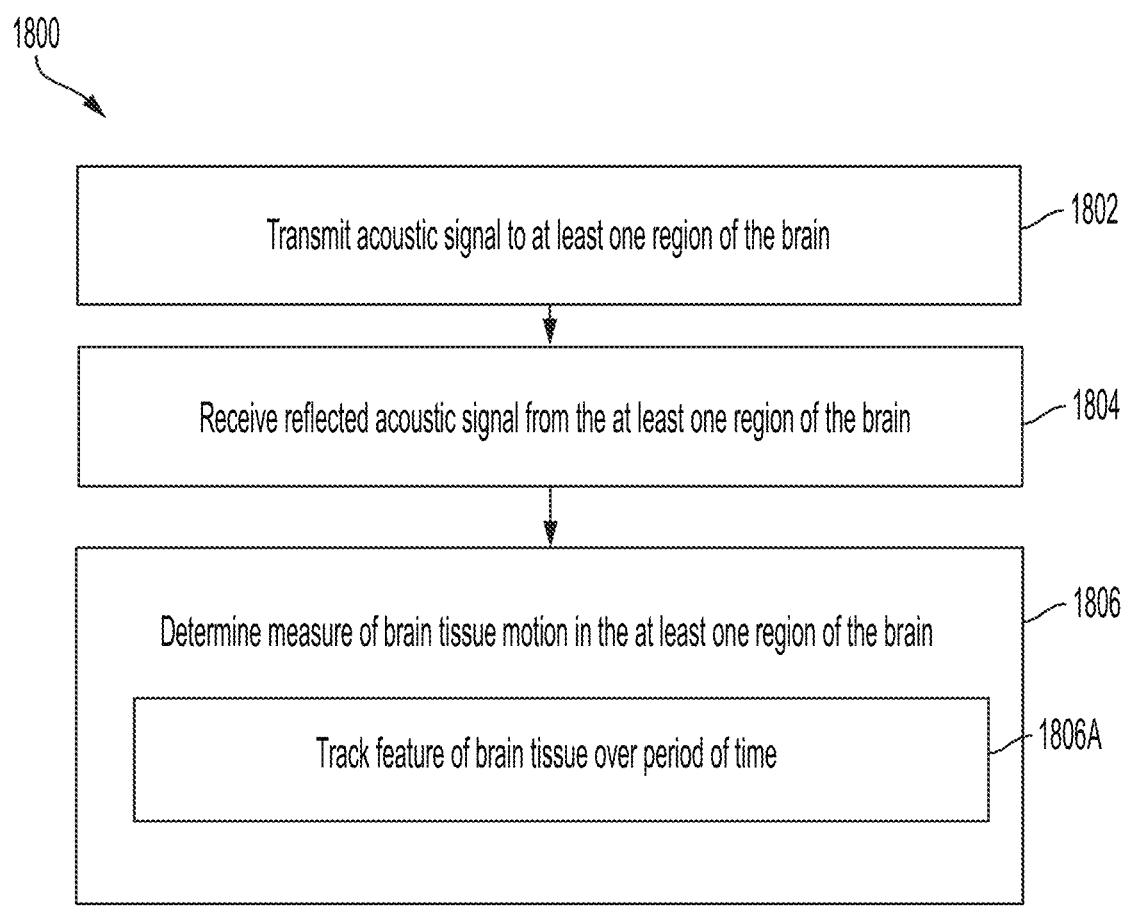
FIG. 18 shows an illustrative process for determining a measure of brain tissue motion in a brain via tissue tracking, according to some embodiments.

In some embodiments, one or more tissue tracking techniques may be used to extract brain beat signals is to track tissue movement. FIG. 18 shows an illustrative process for determining a measure of brain tissue motion in a brain via tissue tracking, according to some embodiments The process 1800 may begin at act 1802. Acts 1802-1806 may be performed in the same manner as acts 902-906 of process 900.

At act 1806A, the measure of brain tissue motion in the at least one region of the brain may be determined at least in part by tracking a feature of brain tissue over a period of time.

The brain is a three-dimensional structure, however, the typical brightness (B-mode) image can capture only a two-dimensional slice of that image at a time. Accordingly, the inventors have recognized that in order to accurately perform tissue tracking, image features that are known have some representation in the imaging plane at all times must be tracked. For example, brain ventricles may provide a good landmark for this purpose.

In addition, tissue motion can be subtle and hence invisible due to low spatial resolution. Accordingly, the tissue tracking techniques described herein take into consideration techniques for overcoming the low spatial resolution of B-mode images which may render tissue motion imperceptible.

i. Finite Difference Techniques/Correlation of Consecutive Frames

As described herein, tracking the exact location of tissue may be difficult to achieve. As an alternative, in some embodiments, the image similarity and/or differences over time may be tracked.

Figure 19:
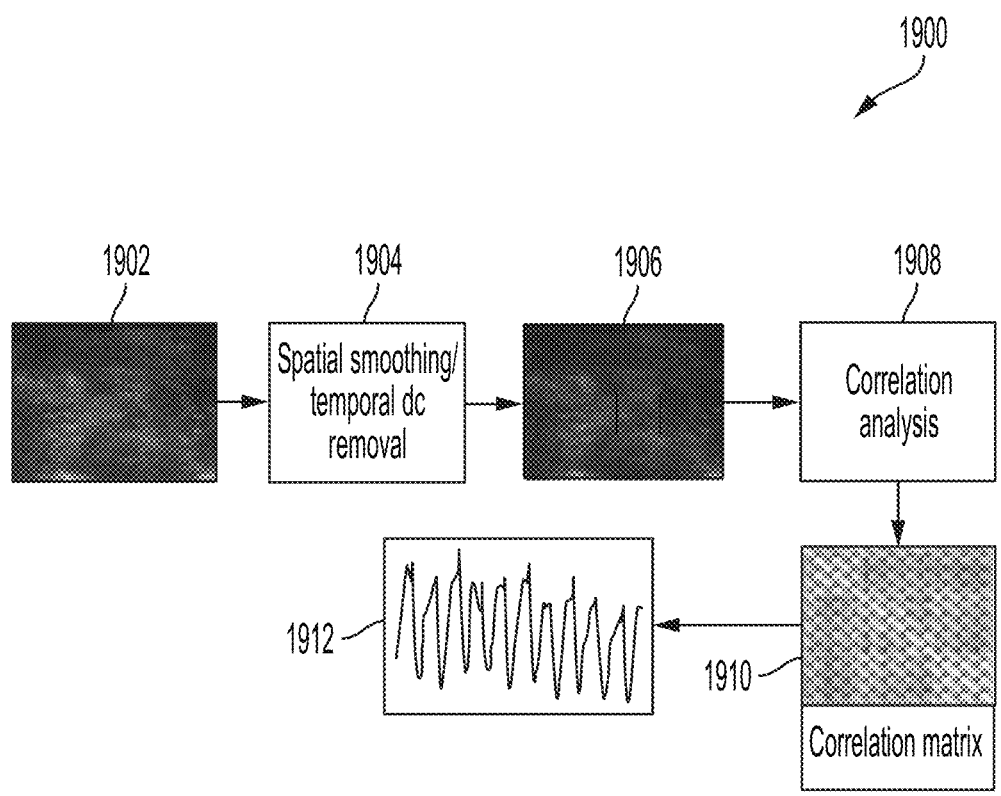
FIG. 19 shows an example flow diagram of tissue tracking using finite differences, according to some embodiments.

FIG. 19 shows an example flow diagram of tissue tracking using finite differences, according to some embodiments. The process illustrated in flow diagram 1900 may begin at act 1902 where a set of ultrasound images is obtained. The set of ultrasound images may comprise at least two images. In some embodiments, the set of ultrasound images comprises a plurality of B-mode images.

At act 1904, the set of ultrasound images is "cleaned" using spatial smoothing at every frame. In some embodiments, a dc blocker may additionally or alternatively be used to remove the bias and shifts and drifts in the extracted signal.

At act 1906, a region of interest in the set of ultrasound images may be identified. The set of ultrasound images may be cut (e.g., cropped) based on the identified region of interest. As described herein, the region of interest may include features that are known to have some representation in the imaging plane at all times. For example, in some embodiments, the region of interest may include one or more ventricles.

At act 1908, a correlation matrix may be computed. For example, the correlation matrix may reflect a correlation between the set of ultrasound images. In some embodiments, the correlation matrix may reflect a correlation between behavior of a feature tracked over time through the set of ultrasound images.

At act 1910, a row of the correlation matrix may be selected as a beating representation of brain tissue depicted in the set of ultrasound images. The temporal oscillatory behavior of the tissue may be reflected in the structured correlation matrix. Beating follows an oscillatory behavior, which may be captured through comparing a template to the sequence of frames recorded in the set of B-mode images.

Accordingly, motion of the brain tissue may be extracted from the set of ultrasound images using the process 1900. Plot 1912 illustrates an example signal of brain tissue motion extracted from the set of ultrasound images by performing process 1900.

ii. Ventricle Beat Tracking

In some embodiments, a ventricle beat tracking technique may be implemented track tissue motion. For example, contraction and expansion of ventricles in the brain may be tracked. As mentioned before, tracking individual pixels may not be feasible in some instances to low spatial resolution. To overcome this, a ventricle's contractions and/or expansions may be tracked instead in order to capture the brain beat. In some embodiments, this ventricle tracking may be performed one-dimensionally, by measuring the distance between ventricle walls over time. In some embodiments, ventricle tracking may be performed two-dimensionally, by measuring changes in surface area of the ventricle. In some embodiments, ventricle tracking may be performed in three-dimensions, by measuring the ventricle volume.

Figure 20:
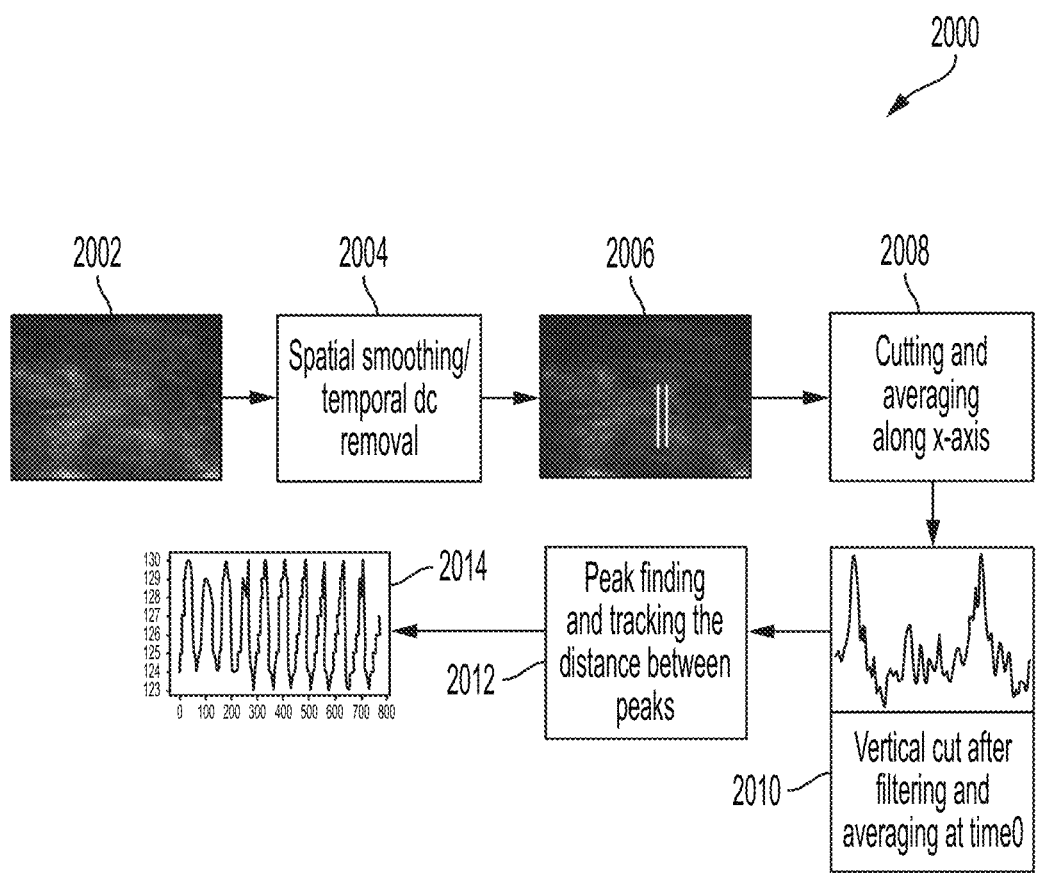
FIG. 20 shows an example flow diagram of ventricle edge tracking for brain beat extraction, according to some embodiments.

FIG. 20 shows an example flow diagram of ventricle edge tracking for brain beat extraction, according to some embodiments. FIG. 20 presents an initial assessment of the one-dimensional case for ventricle tracking. At act 2002, a set of ultrasound images is obtained. The set of ultrasound images may comprise at least two images. In some embodiments, the set of ultrasound images comprises a plurality of B-mode images.

At act 2004, the set of ultrasound images is "cleaned" using spatial smoothing at every frame. At act 2006, a dc blocker may be used to remove the bias and shifts and drifts in the extracted signal.

Figure 21:
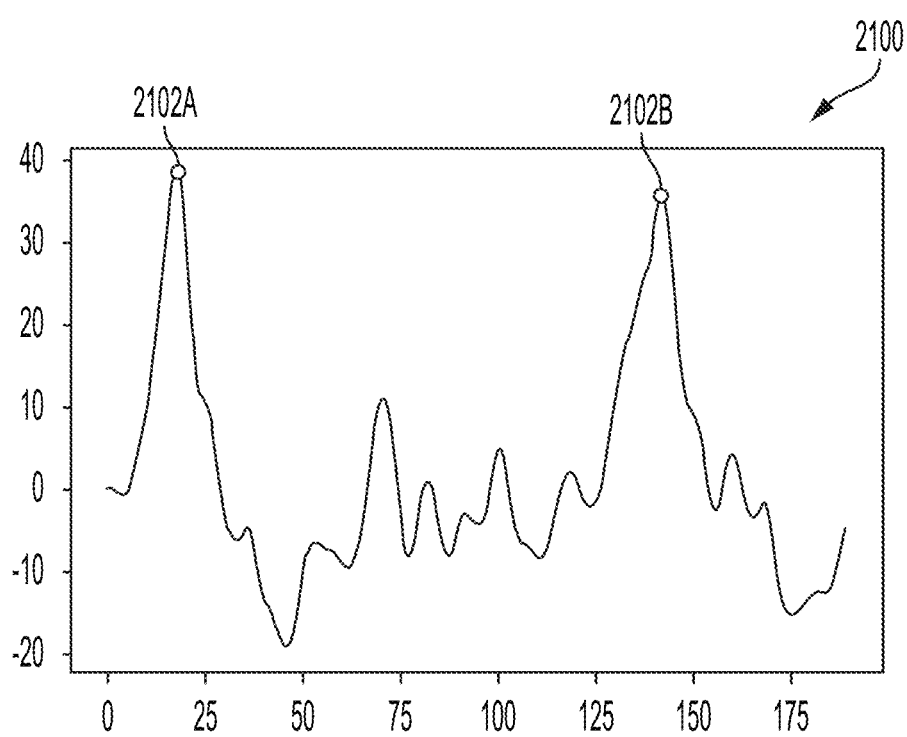
FIG. 21 shows an example of ventricle wall detection, according to some embodiments.

At act 2008, each frame is cut into segments that include the ventricle upper and lower wall. Multiple neighboring beams may be averaged to improve signal to noise ratio. In general, ventricle walls are relatively brighter than background. This leads to two peaks 2102A, 2102 in the extracted signal at every timestep which represent ventricle walls, as shown in the plot 2100 of FIG. 21. Plot 2100 mat be generated at act 2010. FIG. 21 shows an example of ventricle wall detection, according to some embodiments.

At act 2012, the distance between these peaks is tracked to extract the ventricle beat signal. The extracted wave shape here is in terms of beam sample depth, which is measurable in millimeters.

Figure 22:
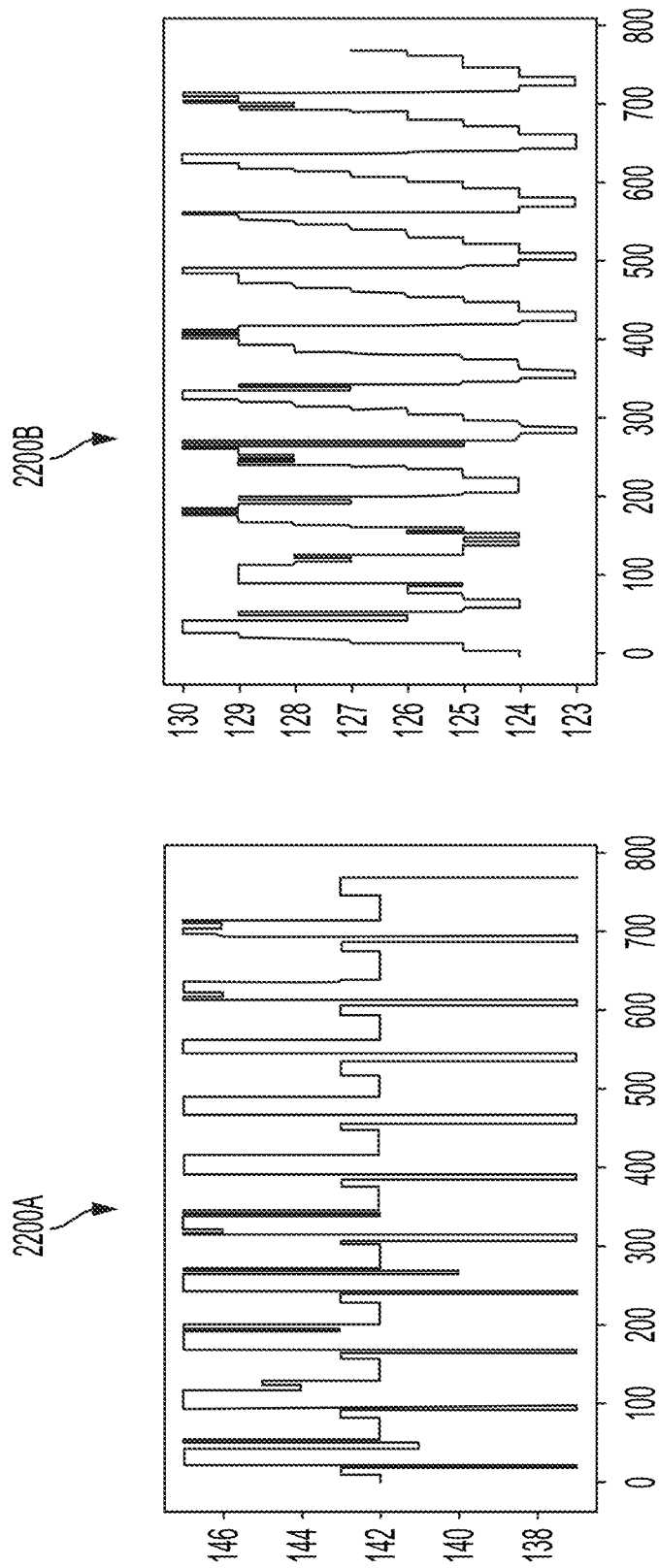
FIG. 22 show examples of sample beat signals extracted from different regions of the ventricle, according to some embodiments.

The number of beams selected to average at act 2008, has an adverse effect on extracted signal shape. Two examples 2200A, 2200B are shown in FIG. 22. FIG. 22 show examples 2200A, 2200B of sample beat signals extracted from different regions of the ventricle, according to some embodiments. Accordingly, in some embodiments, two-dimensional and/or three-dimensional ventricle tracking techniques which track surface area or volume are used which may lead to a more robust extraction of tissue motion.

d. Spectral Clustering

Finding patterns in B-mode frame sequences may be sensitive to spatial location. The inventors have recognized that groups of pixels in different spatial locations may have a synchronous behavior, while immediate neighbors might show a completely different pattern. Accordingly, averaging closeby pixels to extract temporal patterns from B-mode frame sequences may not be possible.

Instead, the inventors have developed a system that performs spatiotemporal clustering to group pixels together and extracts a spatial and temporal pattern in B-mode images from those clusters.

Figure 23:
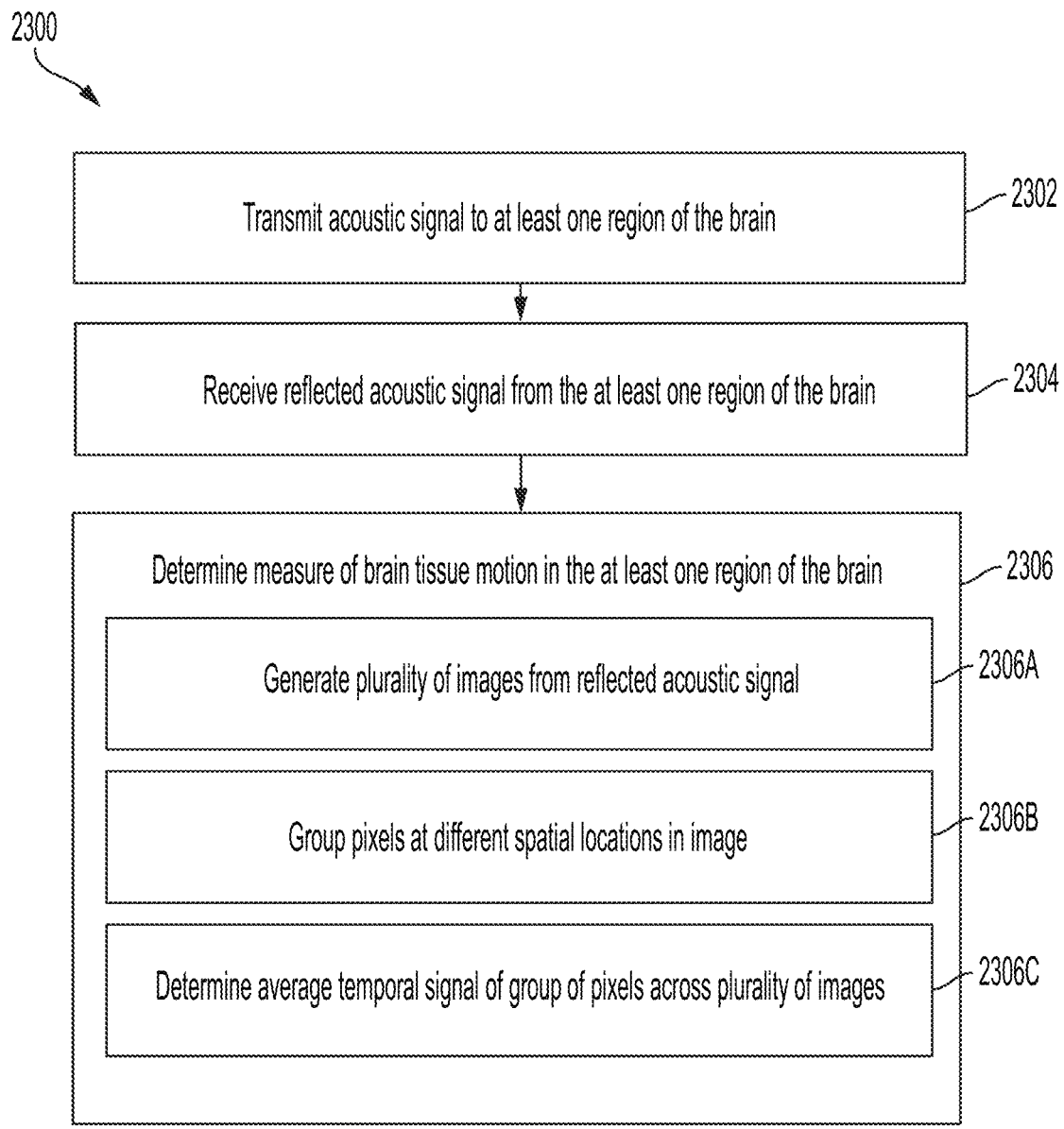
FIG. 23 shows an illustrative process for determining a measure of brain tissue motion in a brain via spectral clustering, according to some embodiments.

FIG. 23 shows an illustrative process for determining a measure of brain tissue motion in a brain via spectral clustering, according to some embodiments.

The process 2300 may begin at act 2302. Acts 2302-2306 may be performed in the same manner as acts 902-906 of process 900.

At acts 2306A-2306C, the measure of brain tissue motion in the at least one region of the brain may be determined at least in part by performing spectral clustering. For example, as described herein, a plurality of images may be generated from the reflected acoustic signal at act 2306A. In some embodiments, the plurality of images may comprise B-mode ultrasound images.

At act 2306B, pixels of a respective image of the plurality of image may be grouped together. The pixels may be located at different spatial locations in the image. In particular, the pixels grouped together may not be neighboring pixels. Instead, the pixels may be grouped based on their exhibiting the same behavior in the image.

At act 2306C, an average temporal signal of the group of pixels clustered together at act 2306B may be determined. In some embodiments, act 2306C may be performed for multiple groups of clustered pixels.

Figure 24:
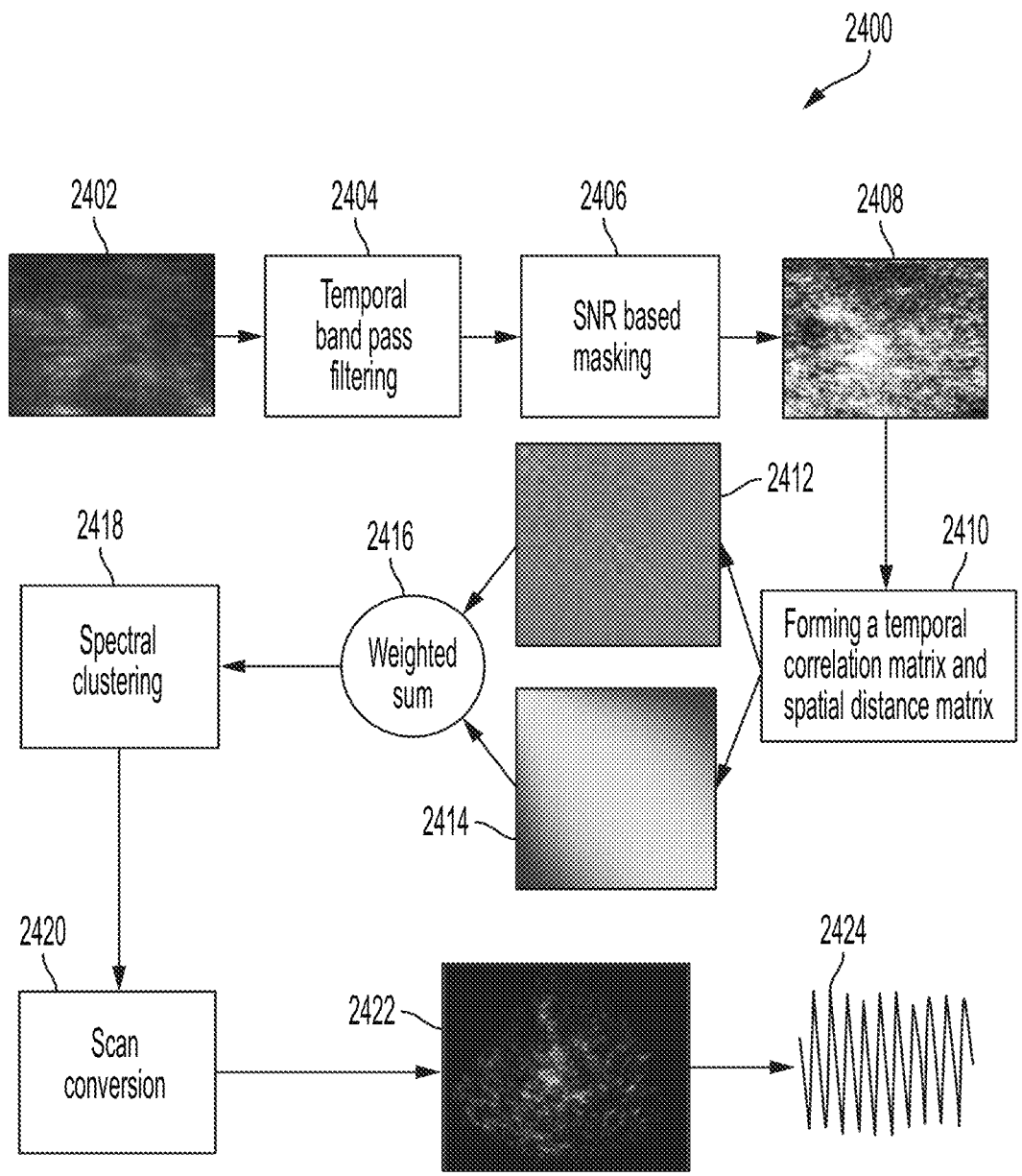
FIG. 24 shows an example flow diagram of spatiotemporal clustering, according to some embodiments.

FIG. 24 shows an example flow diagram of spatiotemporal clustering, according to some embodiments.

To perform spatiotemporal clustering task, a set of ultrasound images may first be obtained at act 2402. The set of ultrasound images may comprise at least two images. In some embodiments, the set of ultrasound images may comprise a plurality of B-mode images.

At act 2404, the set of ultrasound images may be "cleaned" by applying a band pass filter to the signal. For example, in some embodiments, a bandpass filter with a passband of [0.3, 10] Hz may be applied.

At act 2406, the pixels may be masked using a signal to noise ratio (SNR) mask. Act 2408 shows the resulting images. It may be assumed that the signal of interest should have the maximum power in the frequency range of [0.3, 3] Hz.

At act 2410, a correlation matrix 2412 between different pixel time series may be estimated. A spatial distance matrix 2414 may also be computed at act 2410 to keep the pixels spatially contiguous. There is a tradeoff between the temporal correlation matrix and distance matrix, however this may be controlled by using a weighted sum, at act 2416.

At act 2418, spectral clustering may be performed. For example, pixels exhibiting a synchronous behavior may be clustered so that a temporal pattern can be extracted from the cluster.

At acts 2420-2422, averaged temporal signal for the cluster can be computed to estimate the brain beat signal. Plot 2424 illustrates the extracted motion signal.

In some embodiments, the spectral clustering techniques described herein may be used in combination with one or more other techniques. For example, in some embodiments, the spectral clustering techniques described herein may be used in combination with one or more of the signal decomposition techniques described herein (e.g., to decompose each cluster into temporal components).

V. Example Applications of Pulsatility Mode Sensing a. Brain Health Metrics

The inventors have recognized that the pulsatility mode measurements obtained according to the techniques described herein may facilitate determination of a number of metrics that may be used to assess brain health. For example, in some embodiments, the pulsatility mode measurements obtained according to the techniques described herein may be used to determine a measure of intracranial pressure, cerebral blood flow velocity (CBFV), intracranial elastance and/or beating (pulsatility) of the brain.

Figure 25:
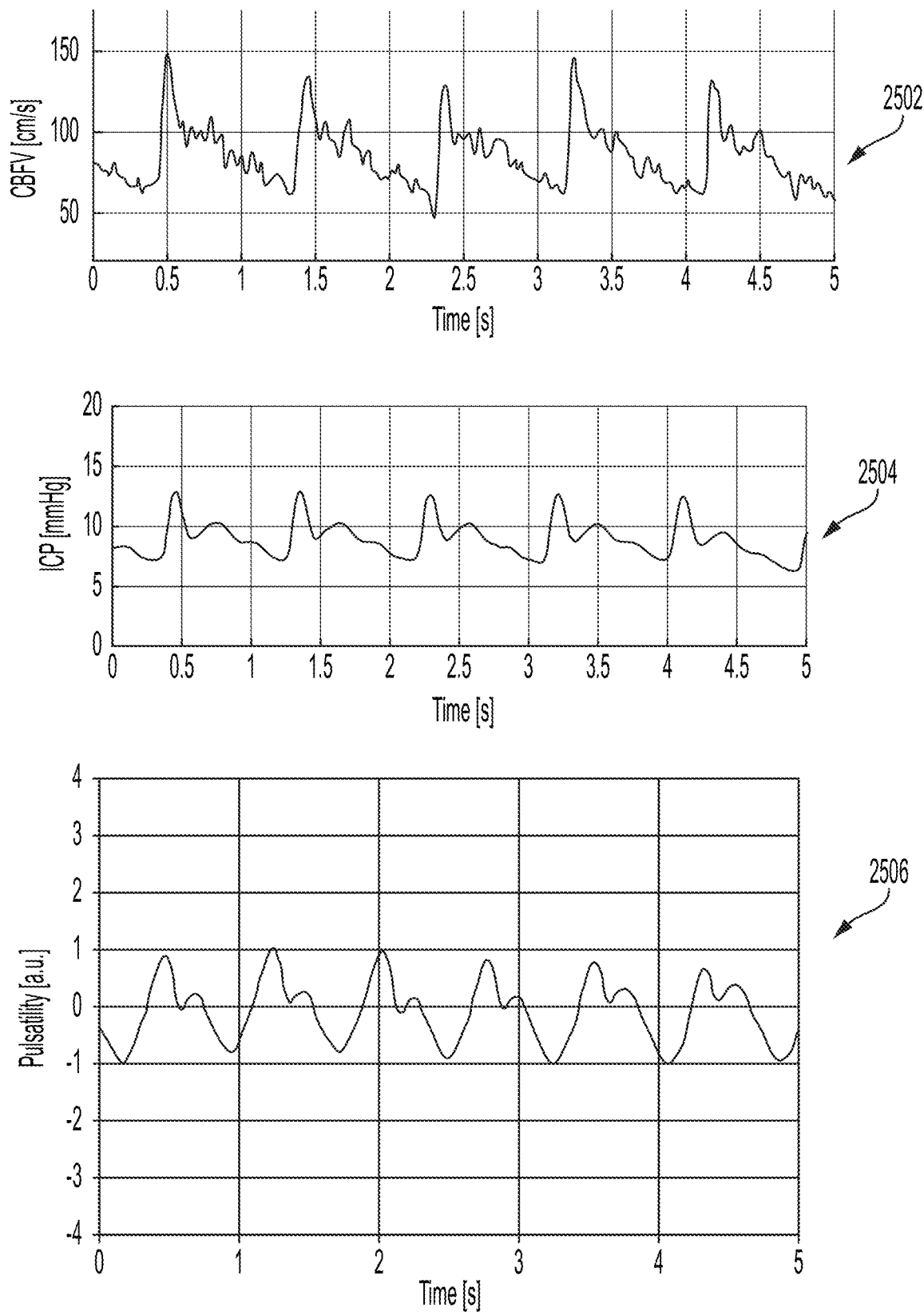
FIG. 25 shows example cerebral blood flow, intracranial pressure, and pulsatility waveforms, according to some embodiments.

The techniques described herein assume that the heart acts as an endogenous mechanical driver that induces motion over the cardiac cycle in the brain. This motion subsequently leads to transient changes in the blood flow and pressure in the brain. These waveforms are synchronous with the arterial pulse. Exemplary data is shown in FIG. 25. In particular, FIG. 25 shows example plots of cerebral blood flow 2502, intracranial pressure 2504, and pulsatility 2506 waveforms, according to some embodiments.

Figure 26:
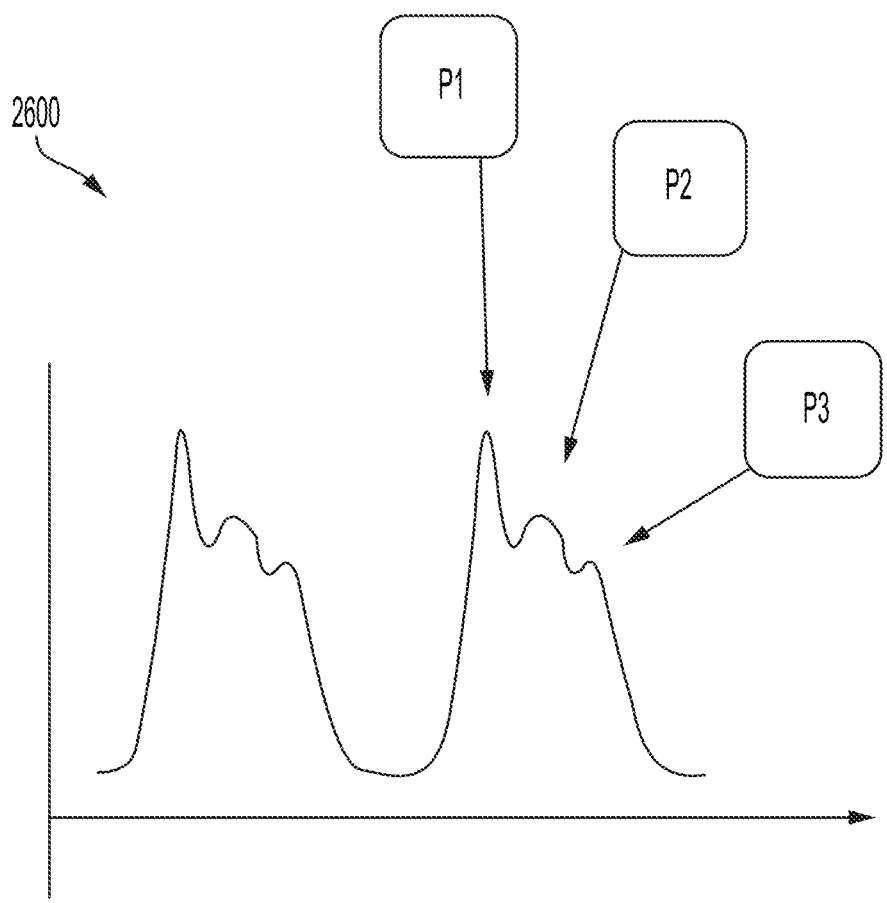
FIG. 26 shows a representative intracranial pressure trifid waveform, according to some embodiments.

In healthy subjects, ICP waveforms are trifid: there are three distinct peaks, which correlate to the arterial pressure. All these waves are rarely more than 4 mmHg in amplitude, or 10-30% of the mean ICP. FIG. 26 shows a representative intracranial pressure trifid waveform 2600, according to some embodiments.

The P1 wave, also known as the percussion wave, correlates with the arterial pulse transmitted through the choroid plexus into the CSF. It will lag slightly behind the arterial transducer. The P2 wave, also known as the tidal wave, represents cerebral compliance. It can be thought of as a "reflection" of the arterial pulse wave bouncing off the springy brain parenchyma. The P3 wave, also known as the dicrotic wave, correlates with the closure of the aortic valve, which makes the trough prior to P3 the equivalent of the dicrotic notch.

Changes in the shape of the ICP waveforms, i.e., P1, P2, and P3, correlate with different brain conditions. For example, increasing amplitude of all waveforms suggests rising intracranial pressure, decreasing amplitude of the P1 waveform suggests decreased cerebral perfusion, increasing amplitude of the P2 waveform suggests decreased cerebral compliance. "Plateau" waves suggest intact cerebral blood flow autoregulation, etc.

These changes manifest in the form of low frequency tissue strain, which due to its dynamic nature, leads to different temporal patterns of pulsatility in brain tissue (aka tissue motion) and pulsatility in cerebral blood flow.

According to some aspects of the technology, there is provided methods for measuring the changes in the pulsatility behaviors and correlating them to metrics of brain health including ICP, cerebral blood flow, and ICE. Such an approach enables the characterization of brain tissue integrity in a wide range of neurological diseases in which changes in the biomechanical properties of the brain can lead to dramatic changes in pressure and flow dynamics, and hence tissue motion. Such techniques also provide a fast means of revealing subtle physiological variations of the brain and potentially other tissues.

Figure 27:
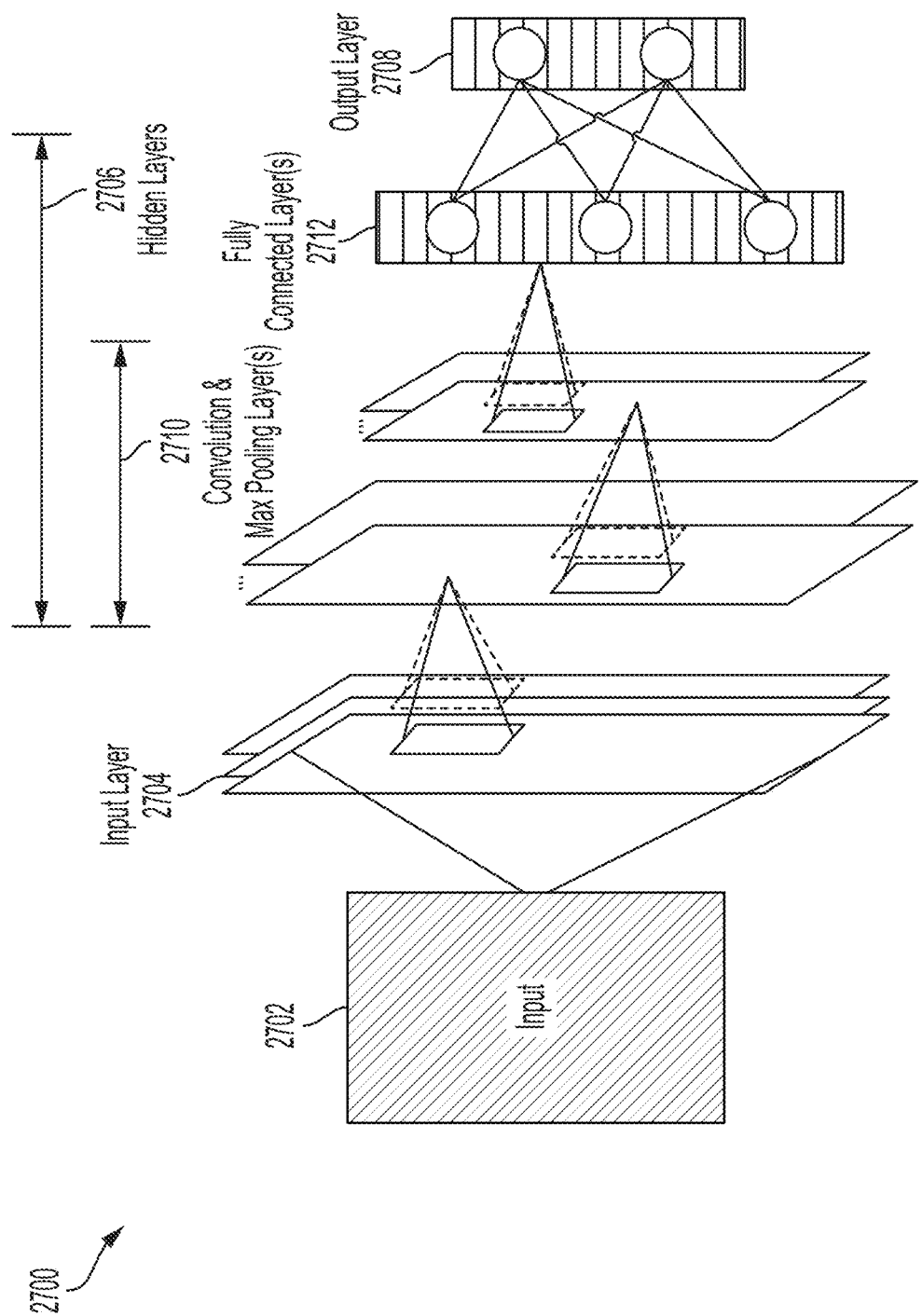
FIG. 27 shows an example machine learning neural network for extracting intracranial pressure using pulsatility mode sensing.

In some embodiments, the methods may be performed using one or more machine learning algorithms. The machine learning algorithms can be in the form of a classification or regression algorithm, which may include one or more sub-components such as convolutional neural networks, recurrent neural networks such as LSTMs and GRUs, linear SVMs, kernel SVMs, linear and/or nonlinear regression, and various techniques from unsupervised learning such as variational autoencoders (VAE), generative adversarial networks (GANs) which are used to extract relevant features from the raw input data and partially supervised learning methods such as self-supervised learning, semi-supervised learning and reinforcement learning which learn the transfer functions either with limited labels or through extracting correlation and causality for existing data. FIG. 27 shows an example machine learning neural network 2700 for extracting intracranial pressure using pulsatility mode sensing.

As shown in FIG. 27, the example machine learning neural network 2700 may include a plurality of layers. An input layer 2704 is provided for receiving input data 2702. When training the example machine learning neural network 2700, as described herein, the input 2702 may comprise training data. When using the example machine learning neural network 2700 to obtain new information, the input 2702 may comprise, in some embodiments, a spatiotemporal p-mode signal, as described herein. An output layer 2708 is provided for outputting information generated by the example machine learning neural network 2700.

Between the input layer 2704 and the output layer 2708, a number of additional layers may be provided. For example, one or more hidden layers 2706, one or more convolution and max pooling layers 2710, and one or more fully connected layers 2712 may be provided. The one or more fully connected layers 2712 may comprise multiple nodes, each node being connected to each node of the output layer 2708, as shown in FIG. 27.

The techniques described herein may use training data collected from a cohort of patients. The data may be used to "train" the machine learning model. This model may then be used to infer where to optimally steer an ultrasound beam and detect, monitor, or localize brain conditions during the "test" time. The same model may be further employed with techniques such as reinforcement learning to continuously learn and adapt to a patient's normal and abnormal brain activities. In some aspects, the training data can be generated using machine learning techniques such as VAE and GANS and/or physics based in-silico (simulation-based) models.

In some embodiments, input for the machine learning model may be the spatiotemporal p-mode signals obtained according to the techniques described herein, or features extracted thereof. The model may output a performance metric constructed based on the numeric values and time-waveforms of benchmark ICP-ICE data (e.g., invasive ICP sensors).

b. Epilepsy and Seizure

In some embodiments, pulsatility mode measurements may be used to predict, monitor, and/or treat Epilepsy and seizures. Epilepsy is a group of neurological disorders characterized by epileptic seizures. Epileptic seizures are episodes that can vary from brief and nearly undetectable periods to long periods of vigorous shaking. These episodes can result in physical injuries, including occasionally broken bones. In epilepsy, seizures tend to recur and have no immediate underlying cause. The cause of most cases of epilepsy is unknown. Some cases occur as the result of brain injury, stroke, brain tumors, infections of the brain, and birth defects through a process known as epileptogenesis. Epileptic seizures are the result of excessive and abnormal neuronal activity in the cortex of the brain. The diagnosis involves ruling out other conditions that might cause similar symptoms, such as fainting, and determining if another cause of seizures is present, such as alcohol withdrawal or electrolyte problems. This may be partly done by imaging the brain and performing blood tests. Epilepsy can often be confirmed with an electroencephalogram (EEG).

The diagnosis of epilepsy is typically made based on observation of the seizure onset and the underlying cause. An electroencephalogram (EEG) to look for abnormal patterns of brain waves and neuroimaging (CT scan or MRI) to look at the structure of the brain are also usually part of the workup. While figuring out a specific epileptic syndrome is often attempted, it is not always possible. Video and EEG monitoring may be useful in difficult cases. An electroencephalogram (EEG) can assist in showing brain activity suggestive of an increased risk of seizures. It is only recommended for those who are likely to have had an epileptic seizure on the basis of symptoms. In the diagnosis of epilepsy, electroencephalography may help distinguish the type of seizure or syndrome present.

Accordingly, in some embodiments, pulsatility mode measurements may be used in addition or alternative to the methods described herein for predicting, monitoring, and/or treating Epilepsy and seizures. Pulsatility mode measurements provide a more accurate, cost-efficient, and non-invasive method of predicting, monitoring, and/or treating Epilepsy and seizures.

VI. Example Computing Systems

Figure 28:
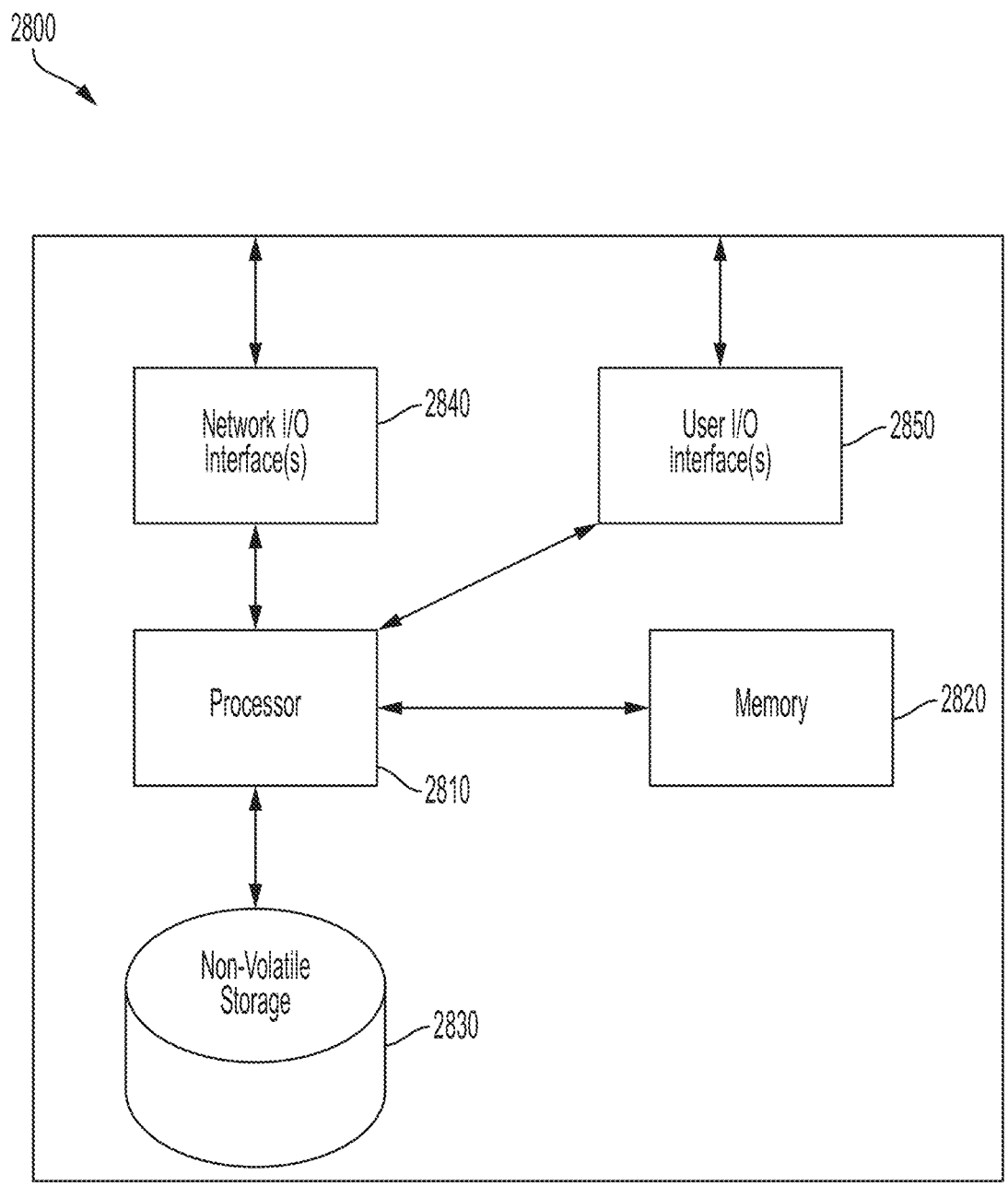
FIG. 28 is a block diagram of an exemplary computer system in which aspects of the present disclosure may be implemented, according to some embodiments.

FIG. 28 shows a block diagram of an example computer system 2800 that may be used to implement embodiments of the technology described herein. The computing device 2800 may include one or more computer hardware processors 2802 and non-transitory computer-readable storage media (e.g., memory 2804 and one or more non-volatile storage devices 2806). The processor(s) 2802 may control writing data to and reading data from (1) the memory 2804; and (2) the non-volatile storage device(s) 2806. To perform any of the functionality described herein, the processor(s) 2802 may execute one or more processor-executable instructions stored in one or more non-transitory computer-readable storage media (e.g., the memory 2804), which may serve as non-transitory computer-readable storage media storing processor-executable instructions for execution by the processor(s) 2802.

VII. Equivalents and Scope

Embodiments of the above-described techniques can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the technology described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the technology described herein. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present technology as described above. As used herein, the term "computer-readable storage medium" encompasses only a computer-readable medium that can be considered to be a manufacture (i.e., article of manufacture) or a machine. Alternatively or additionally, the technology described herein may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of technology described herein. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present technology may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, examples of which have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various events/acts are described herein as occurring or being performed at a specified time. One of ordinary skill in the art would understand that such events/acts may occur or be performed at approximately the specified time.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately," "substantially," and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of the technology, it is to be appreciated that various alterations, modifications, and improvements will readily occur to those skilled in the art.

Such alterations, modifications, and improvements are intended to be part of this disclosure, and are intended to be within the spirit and scope of the disclosure. Further, though advantages of the present technology are indicated, it should be appreciated that not every embodiment of the technology will include every described advantage. Some embodiments may not implement any features described as advantageous herein and in some instances. Accordingly, the foregoing description and drawings are by way of example only.

What is claimed is:

1. A system configured to determine a measure of surface area brain tissue motion in a brain, the system comprising:
   a monitoring station positioned at a patient bedside;
   at least one wearable beamforming transducer configured to transmit an acoustic signal across a surface area of brain tissue and receive a subsequent acoustic signal from the surface area of the brain tissue; and
   a housing containing at least one processor, the at least one processor configured to:
      determine the surface area brain tissue motion by processing the subsequent acoustic signal, wherein processing the subsequent acoustic signal comprises filtering the subsequent acoustic signal using a spatiotemporal filter;

wherein the spatiotemporal filter uses a singular value decomposition from a plurality of images generated from the subsequent acoustic signal; and wherein the monitoring station, the wearable beamforming transducer, and the separate housing are wirelessly connected.

* * * * *